(12) United States Patent
Lengyel et al.

(10) Patent No.: US 12,201,328 B2
(45) Date of Patent: Jan. 21, 2025

(54) BONE ANCHOR HEAD EXTENDER

(71) Applicant: OrthoPediatrics Corp., Warsaw, IN (US)

(72) Inventors: Rebecca Boerigter Lengyel, Fort Wayne, IN (US); Ryan Harper, Warsaw, IN (US); Scott Lubensky, Warsaw, IN (US); David Wayne Daniels, Winona Lake, IN (US); Collin Gibbs, Columbia City, IN (US); Scott J. Luhmann, Ladue, MO (US)

(73) Assignee: OrthoPediatrics Corp., Warsaw, IN (US)

(*) Notice: Subject to any disclaimer, the term of this patent is extended or adjusted under 35 U.S.C. 154(b) by 80 days.

(21) Appl. No.: 18/076,379

(22) Filed: Dec. 6, 2022

(65) Prior Publication Data

US 2023/0098136 A1 Mar. 30, 2023

Related U.S. Application Data

(63) Continuation of application No. 17/413,481, filed as application No. PCT/US2019/066061 on Dec. 12, 2019, now Pat. No. 11,547,453.

(60) Provisional application No. 62/778,663, filed on Dec. 12, 2018.

(51) Int. Cl.
*A61B 17/70* (2006.01)
*A61B 17/86* (2006.01)

(52) U.S. Cl.
CPC ...... *A61B 17/7032* (2013.01); *A61B 17/8685* (2013.01)

(58) Field of Classification Search
CPC .............. A61B 17/7032; A61B 17/8685
USPC ................................. 606/250–279
See application file for complete search history.

(56) References Cited

U.S. PATENT DOCUMENTS

| | | | | |
|---|---|---|---|---|
| 7,462,182 B2 * | 12/2008 | Lim | ................... | A61B 17/7086 606/99 |
| 8,758,411 B1 * | 6/2014 | Rayon | ................ | A61B 17/7049 606/259 |
| 2017/0112541 A1 * | 4/2017 | Zhang | ................ | A61B 17/7034 |

* cited by examiner

*Primary Examiner* — Eduardo C Robert
*Assistant Examiner* — Tara Rose E Carter
(74) *Attorney, Agent, or Firm* — Frost Brown Todd LLP

(57) ABSTRACT

A pedicle screw tulip head extender. The extender can include an upper body portion joined to a lower body portion. The upper body portion can have two opposing arms extending upwardly from a curved lower surface to define a substantially U-shaped interior channel having a first channel axis, the curved lower surface defining an access opening extending through the upper body portion in a direction generally perpendicular to the first channel axis. The lower body portion can extend downwardly as a protrusion from the upper body portion and can be joined to the upper body portion and can have first and second sides, the first and second sides being substantially planar and parallel and separated by an interior portion, the first and second sides defining a protrusion height and a protrusion width. A screw can be disposed in the interior portion and have external threads defining a thread diameter greater than the protrusion width.

20 Claims, 21 Drawing Sheets

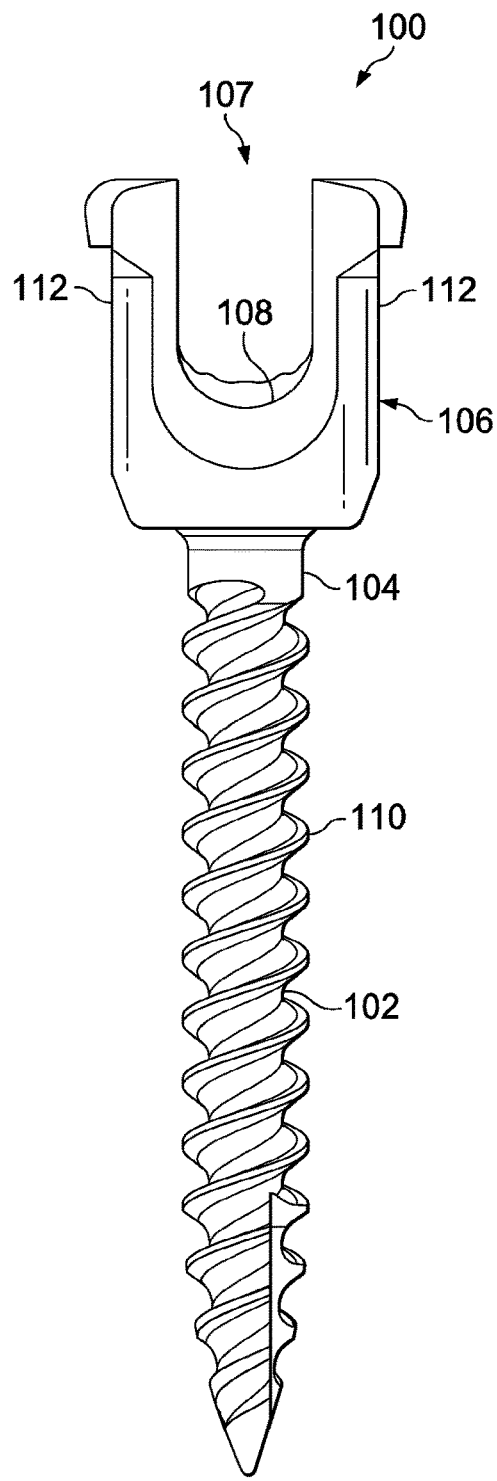
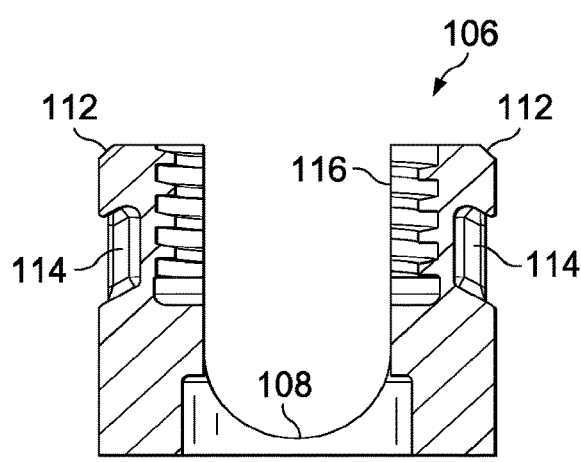
FIG. 1
FIG. 2

BONE ANCHOR HEAD EXTENDER

This application is a continuation of U.S. Non-Provisional application Ser. No. 17/413,481 filed Jun. 11, 2021, which is a National Stage Entry of PCT Application No. PCT/US19/66061 filed Dec. 12, 2019, which claims the priority benefit of U.S. Provisional Patent App. No. 62/778,663 filed Dec. 12, 2018, each of which is incorporated herein by reference in their entirety.

BACKGROUND

Spinal fixation systems may be used to surgically fix, adjust, and/or align the spinal column. One type of spinal fixation system employs a spinal rod for supporting the spine and fixing, adjusting, and/or aligning all or portions of the spinal column into a desired orientation. Attachment of the spinal rod to the spinal column has been achieved using a variety of vertebral anchors. Pedicle screws have been used successfully as vertebral anchors. Pedicle screws and connectors in combination with spinal rods can align and correct deformities in the natural spinal alignment as well as repair traumatic injury. In general, a pedicle screw has a head with a receiving opening into which a spinal rod can be secured.

However, once a pedicle screw is set, i.e., screwed into a portion of the pedicle bone, the location of a spinal rod to be set into it is also set due to the fixed position of the head of the pedicle screw. It can be the case that during the process of spinal fixation it is discovered that the fixed location of the head of the pedicle screw, and, therefore, the fixed location of the reduced spinal rod, is not ideal.

Accordingly, there remains an unmet need for an apparatus, system, and method to provide for variable positioning of a spinal rod in a fixed pedicle screw.

Further, there remains an unmet need for spinal fixation apparatus that permits greater flexibility for neuromuscular and revision cases by providing for a greater variety of instrumentation.

SUMMARY

A bone anchor, such as a pedicle screw, head extender is disclosed. The extender can include an upper body portion joined to a lower body portion. The upper body portion can have two opposing arms extending upwardly from a curved lower surface to define a substantially U-shaped interior channel having a first channel axis, the curved lower surface defining an access opening extending through the upper body portion in a direction generally perpendicular to the first channel axis. The lower body portion can extend downwardly as a protrusion from the upper body portion and can be joined to the upper body portion and can have first and second sides, the first and second sides being substantially planar and parallel and separated by an interior portion, the first and second sides defining a protrusion height and a protrusion width. A screw can be disposed in the interior portion and have external threads defining a thread diameter greater than the protrusion width.

BRIEF DESCRIPTION OF THE DRAWINGS

The present disclosure will be more readily understood from a detailed description of some example embodiments taken in conjunction with the following figures:

FIG. 1 depicts a side elevation view of an example of a pedicle screw.

FIG. 2 depicts a partial cross-sectional view of a head of the pedicle screw of FIG. 1.

DETAILED DESCRIPTION

Figure 3:
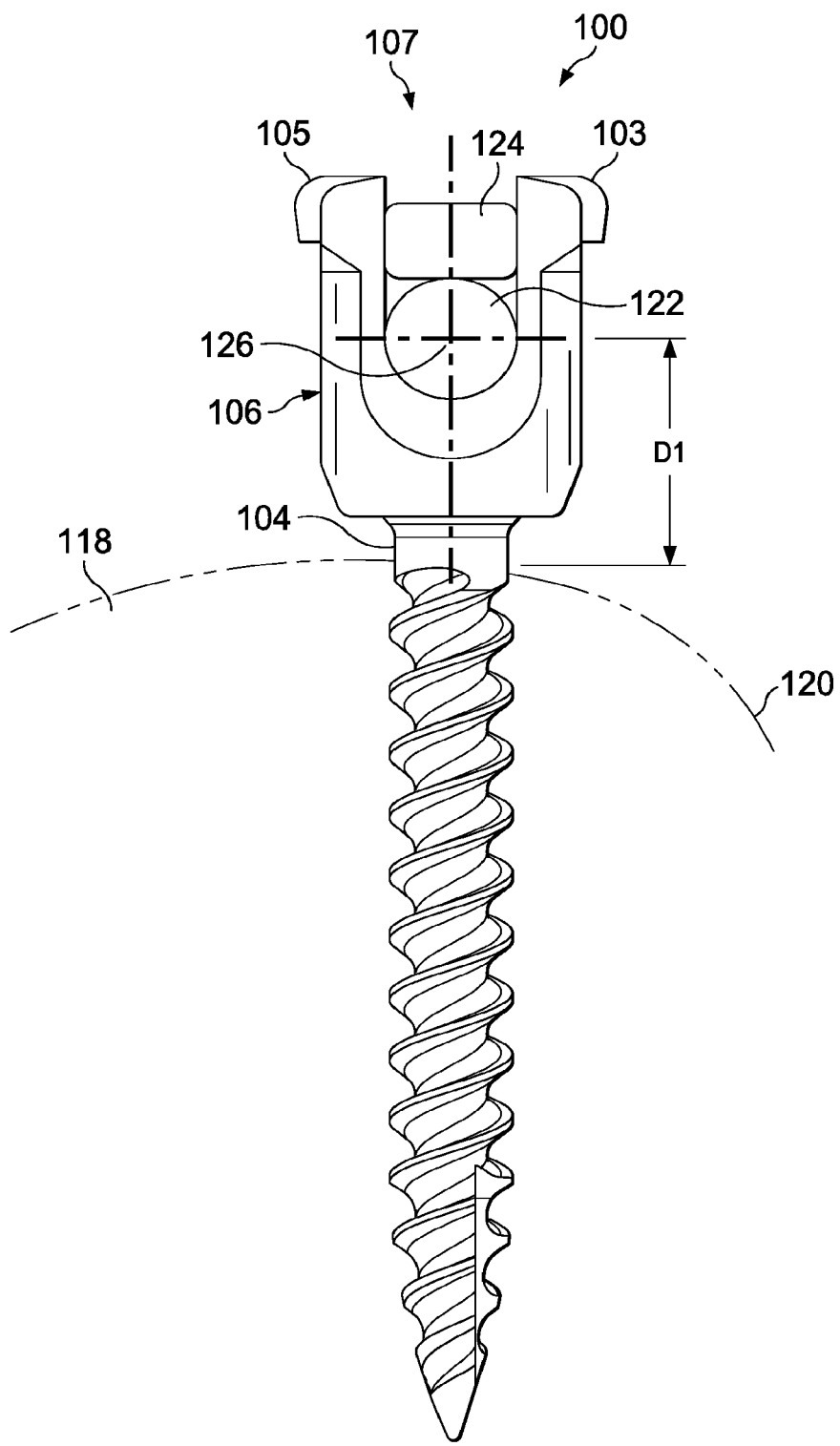
FIG. 3 depicts a schematic representation of a pedicle screw in a bone.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Described herein are example embodiments of bone anchors (e.g., hooks, screws, etc.) useful for orthopedic procedures such as, for example, spinal fixation. In the illustrated embodiments a pedicle screw is disclosed to teach the features of a bone anchor and how the one or more embodiments of tulip head extenders engage and/or work with such illustrative pedicle screws, but the disclosure is not to be limited only to pedicle screws, nor are the tulip head extenders limited to engaging and/or working with only pedicle screws.

Referring to FIG. 1, a representative pedicle screw 100 is shown. Pedicle screw 100 can be any of known pedicle screws with any of known beneficial features for installation and use in processes and systems such as, for example, of spinal fixation. For the purposes of the present disclosure, the pedicle screw is described as including a screw shank 102, a neck 104, a head 106, which is often referred to as a tulip head 106. The tulip head 106 can include first and second tulip arms 112 opposed from each other. First and second tulip arms form a channel 107. First and second tulip arms 112 can extend from a curved lower surface (e.g., rod seat 108) defining the substantially U-shaped interior channel 107. The channel 107 can be constructed to receive a spinal fixation rod (e.g., 122) and can include a channel axis. The channel axis can correspond to, and be coincident with, a longitudinal axis of a spinal fixation rod when it is reduced into the channel 107.

The shank can have an inner diameter and an outer diameter, the inner diameter and outer diameter each being determined by the size of the screw and the depth of threads 110 on shank 102. The thread depth, pitch, and other dimensional features can be predetermined based on the requirements of the pedicle screw, as is known in the art. That is, the proportions of the pedicle screw depicted are for illustrative purposes only and variations in the length, shape, and/or configuration of such pedicle screw may vary such as, for example, the shape and size of the head, the length of the shank, diameter of the screw, thread pitch, thread length, number of thread leads, shank induced compression and the like may be varied without departing from the scope of the disclosure.

Other components and features of a pedicle screw may be included that aid in its insertion into a bone and its use. For example, as depicted in the partial cross-sectional view of tulip head 106 in FIG. 2, tulip head 106 may include features for compatible operation with driving tool (not shown) and a rod reduction device (not shown). As a specific example, a rod reduction device, as is known in the art, may be used to engage with tulip head 106 to urge, or reduce, a spinal fixation rod into the channel 107 and toward the rod seat 108, manipulate one or more vertebrae, and/or insert a set screw for temporary or stationary fixation of the spinal rod into the pedicle screw tulip head 106. For this reason, tulip head 106 can have various features, such as grasping tabs 112 and/or pockets 114, for connectivity and operation of the driving tool, rod reducing tool, and/or other instruments, and internal threads 116 for receiving a set screw or other implants and/or instruments.

Referring now to FIG. 3, there is shown a pedicle screw 100 screwed into a bone 118, the surface of which is representatively depicted by the dashed line 120. Bone 118 can be a pedicle, and pedicle screw 100 can be driven into the pedicle until the neck 104 is adjacent the bone 118. In an embodiment, the pedicle can be undertapped for the appropriate screw size. After the pedicle is undertapped a flexible feeler probe may be used to verify presence of threads in the tapped hole. To measure the length of the hole, a feeler probe is advanced to the floor of the hole and a hemostat is clamped to the feeler probe at the point where it exits the pedicle. The appropriate screw diameter and length may subsequently be selected based on both preoperative measurement and intraoperative observation. The same technique can be repeated for any remaining pedicles that need to be inserted and/or instrumented.

A rod reduction tool can be applied over the tulip head 106 of the screw. In an embodiment, fingers of the rod reduction device can engage the pockets 114 of the pedicle screw tulip head 106. The rod 122 can then be reduced by the rod reduction device to set in rod seat 108. A set screw driver can then be used to introduce a set screw 124. The set screw can be passed through the rod reduction device and rotated until it bottoms out, securing rod 122 into the tulip head 106.

As depicted in FIG. 3, once rod 122 is reduced into tulip head 106 and set screw 124 is set, the distance D1 from bone surface 120 and the axial center 126 of rod 122 is immovably fixed. As illustrated, the distance D1 is shown as extending to the axial center of the rod 122, but for description purposes the dimensions D1, as well as D2 and D3 described below, can be measured to the top or bottom of the rod without departing from the scope of the disclosure.

Figure 4:
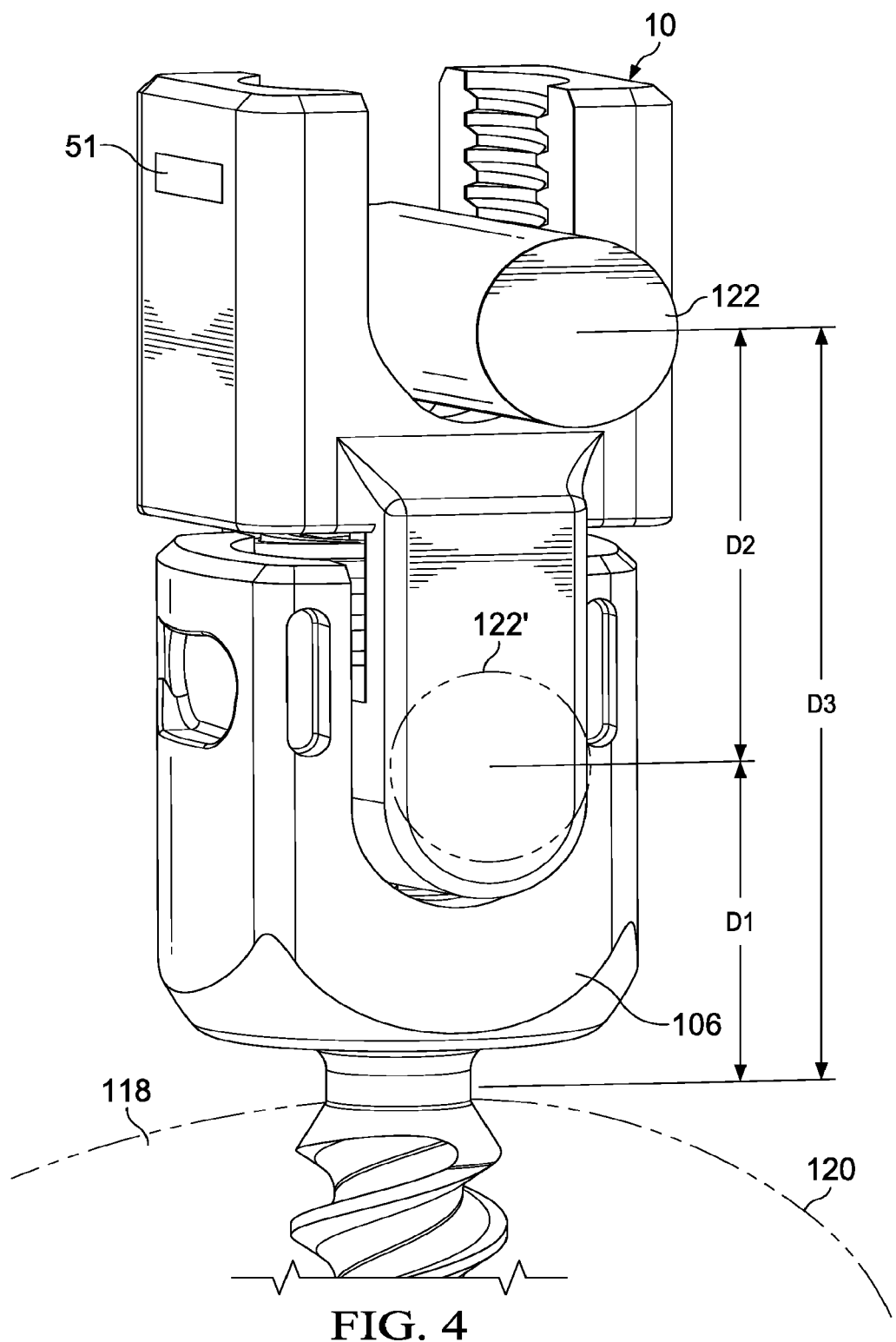
FIG. 4 depicts a perspective view of one example of a pedicle screw extender of the present disclosure engaged with a pedicle screw.

Referring to FIG. 4 there is shown an embodiment of a tulip head extender 10 that, when engaged to and/or installed into tulip head 106, can facilitate the repositioning of rod 122 with respect to bone surface 120 from a distance D1 an additional distance D2, for a total distance D3. As can be understood, extender 10 permits the vertical repositioning of rod 122 from an original position shown as 122' without disturbing pedicle screw 100. The distance D2 can be predetermined by varying the geometry of extender 10, as will be more fully understood in light of the description below.

Figure 5:
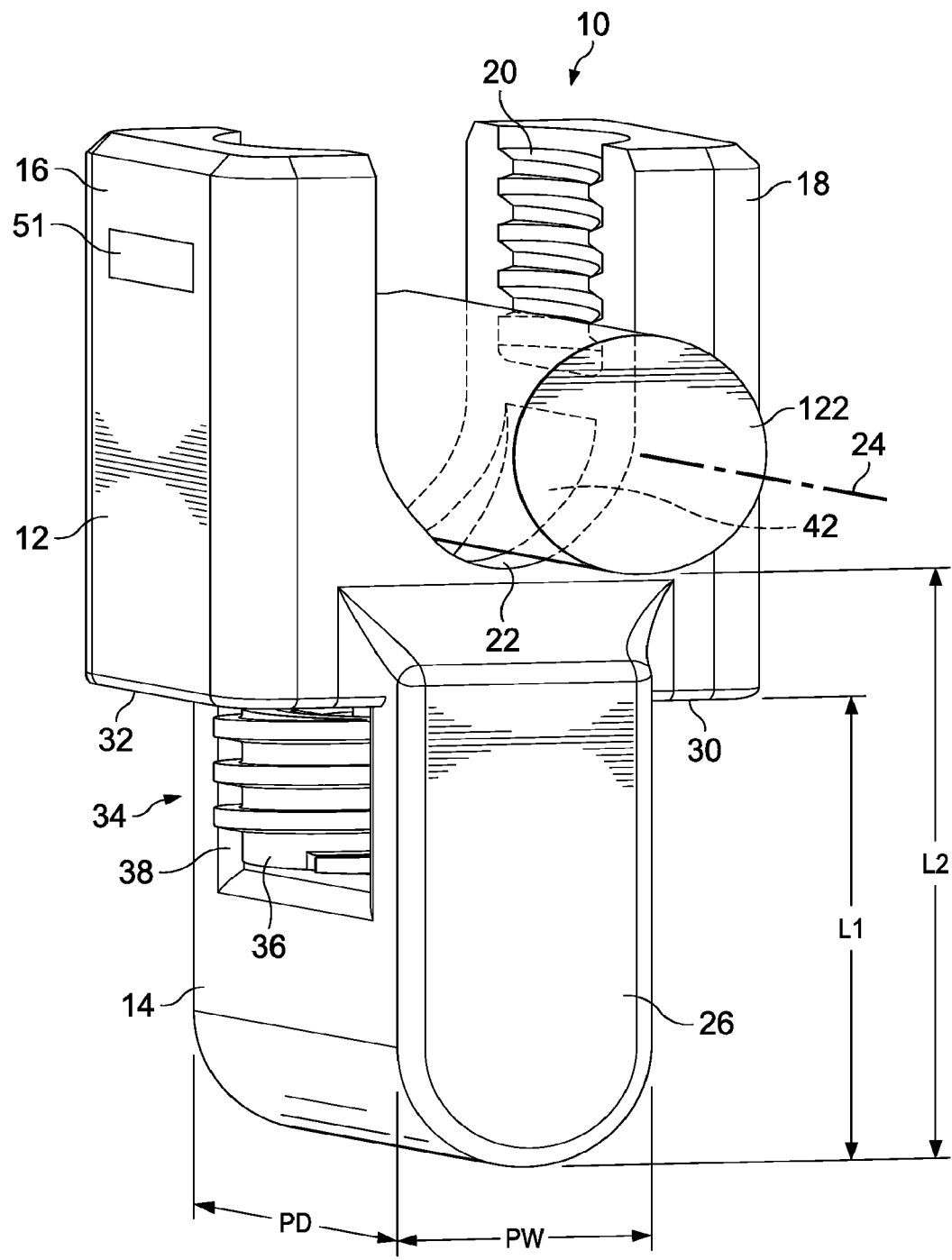
FIG. 5 depicts a perspective view of the pedicle screw extender of FIG. 4.

An embodiment of tulip head extender 10 as shown in FIG. 4 is depicted in more detail in FIG. 5. In the illustrated embodiments, terms such as "vertical," "upper," "lower" "upwardly," and "downwardly" are used in relation to the extender 10 in the orientation shown in the FIGS, and corresponding to the orientation generally experienced in use of pedicle screws and related instrumentation. Extender 10 can have an upper body portion 12 joined to a lower body portion 14. The upper body portion 12 can be integrally formed with lower body portion 14, such as by machining from a blank, injection molding, etc., or the two parts can be manufactured separately and joined by adhesive, welding, press fit, or the like. Upper body portion 12 can have a first extender arm 16 and a second extender arm 18 opposed to the first extender arm. First extender arm 16 and second extender arm 18 can extend from a curved lower surface defining a substantially U-shaped interior channel 22 that can have a first channel axis 24. The first channel axis 24 can correspond to, and be coincident with, a longitudinal axis of a rod 122 when reduced into extender 10. The first interior threads 20 of first and second extender arms can be complementary to receive an appropriately sized set screw (not shown). As can be understood from the description above, first and second extender arms 16 and 18, first interior threads 20, and interior channel 22 correspond to the same or similar functional features of a tulip head, such as tulip head 106 of pedicle screw 100. As can be further understood, the features of the upper portion 12 of extender 10 can include any features 51 desired or required on illustrative bone anchors such as, for example, pockets, tabs, indentations, and openings, to engage with a variety of instruments such as, for example, a particular rod reducing tool, and, as such, facilitate rod reduction by known techniques, albeit reducing the rod a shorter distance than what would have been required to reduce it to the original rod seat 108 (e.g., FIGS. 2 and 3).

Lower portion 14 can extend downwardly from the upper portion 12, and can have a portion sized to fit into the channel 107 and seat on the rod surface 108 of tulip head 106 of pedicle screw 100. That is, lower portion 14 can be a substantially U-shaped protrusion, joined to upper portion 12 by generally parallel spaced apart first and second U-shaped sides, 26 and 28 (side 28 on the side not seen in FIG. 5). First and second U-shaped sides can be substantially identical in size and shape and have a protrusion width PW having a dimension sized according to the channel width of the tulip head 106 of the pedicle screw 100. First and second U-shaped sides can be spaced apart a distance defining a protrusion depth PD, the protrusion depth PD being a dimension suitable for stable securement to the tulip head 106 of pedicle screw 100, and can be predetermined based on the sizing and requirements of related instrumentation. First and second sides 26 and 28 need not be U-shaped, but can have any shape constrained only in that the lower portion 14 be able to be insertable into and seat with the tulip head 106 of a pedicle screw 100 (e.g., channel 107 and seat 108). Thus, first and second sides 26 and 28 can have rectangular shape, for example, and remain functionally capable of being seated into the tulip head 106 of pedicle screw 100.

The extender 10 can have first and second surfaces 30 and 32, which can be generally horizontally oriented portions of the lower surface of upper portion 12, and which can abut the top surface of tulip head 106 of pedicle screw 100 when the extender 10 is set into place. Although in some embodiments, the extender 10 may not have first and second surfaces 30 and 32 or such surface may not be generally horizontally oriented. In some embodiments, first and second sides 26 and 28 can extend a distance L1 below and generally perpendicular to first and second surfaces 30 and 32 to the bottom of the U-shaped sides. Distance L1 can be substantially equal to the depth of the channel having the rod seat 108 of tulip head 106. Curved lower surface 22 of upper portion 12 of extender 10 can be a distance L2 measured from the bottom of the U-shaped first and second sides 26 and 28. Distance L2 can be greater than distance L1, and can be predetermined by design of extender 10 based on the desired distance D3, as shown in FIG. 4.

Lower portion 14 can have an open interior portion 34 defined between first and second U-shaped sides 26 and 28, and in which can be disposed an extender set screw 36. Open interior portion 34 can have open access through a pair of opposing windows 38, 40 (window 40 on the side not seen in FIG. 5) through which the extender set screw 36 may be inserted into and then in its position therein, threads of extender set screw 36 can extend radially outwardly from windows 38, 40. That is, the outside thread diameter of set screw 36 can be greater than the protrusion width PW. This allows the threads of the extender set screw 36 to threadingly engage the inner threads 116 of the first and second tulip arms 112 when the lower portion 14 is inserted into the tulip channel 107, engaging and/or connecting the extender 10 to the tulip head 100. As can be understood from the description herein, extender set screw 36 serves functionally similar to the set screw 124 shown in FIG. 3 to set, however, the extender 10 into the tulip head 106 of pedicle screw 100 as shown in FIG. 4 rather than to set the rod 122 into the tulip head as shown in FIG. 3.

An access opening 42 in upper portion 12 can extend downwardly through the upper portion 12 in a direction generally perpendicular to first channel axis 24. Access opening 42 provides access to the top of extender set screw 36. Extender set screw 36 can have on its top surface a driving portion which can engage with a driver to permit rotation of extender set screw 36 such that its external threads engage the internal threads 116 of tulip head 106, driving the extender set screw down into the tulip channel 107 and connecting the extender 10 to the pedicle screw 100.

Thus, according to the description above with reference to FIGS. 4 and 5, it can be understood that extender 10 can be attached to the tulip head 106 of a pedicle screw 100 to increase the distance from bone surface 120 from a distance having a dimension D1 to a distance having a dimension D3, which is greater than D1. As described, the lower portion 14 of extender 10 can be positioned between the tulip arms 112 and the threads of extender set screw 36 can engage the interior threads 116 of tulip head 106. Extender set screw 36 can be rotated by a driver extending through access opening 42 of extender 10 to connect and/or secure extender 10 to tulip head 106. Once extender is secured to tulip head 106 by tightening extender set screw 36, first and second extender arms 16 and 18, first interior threads 20, and interior channel 22 effectively define a second tulip head into which a spinal fixation rod 122 can be reduced. The distance having a dimension D2 above which a rod would be reduced into tulip head 106 of pedicle screw 100 can be predetermined by adjusting by design the various described components and dimensions. Thus, in operation, a doctor or other operator can choose an extender 10 having dimensions, including dimensions L1 and L2 for the particular pedicle screw 100 being utilized, and the distance D3 that the rod is suspended or positioned over the bone and/or the distance the rod is suspended and/or positioned over the installed pedicle screw. As can be understood, therefore, extender 10 provides great flexibility to increase the rod reduction height relative to bone surface 120 for a fixed position of a tulip head 106 of a fixed pedicle screw 100.

Figure 6:
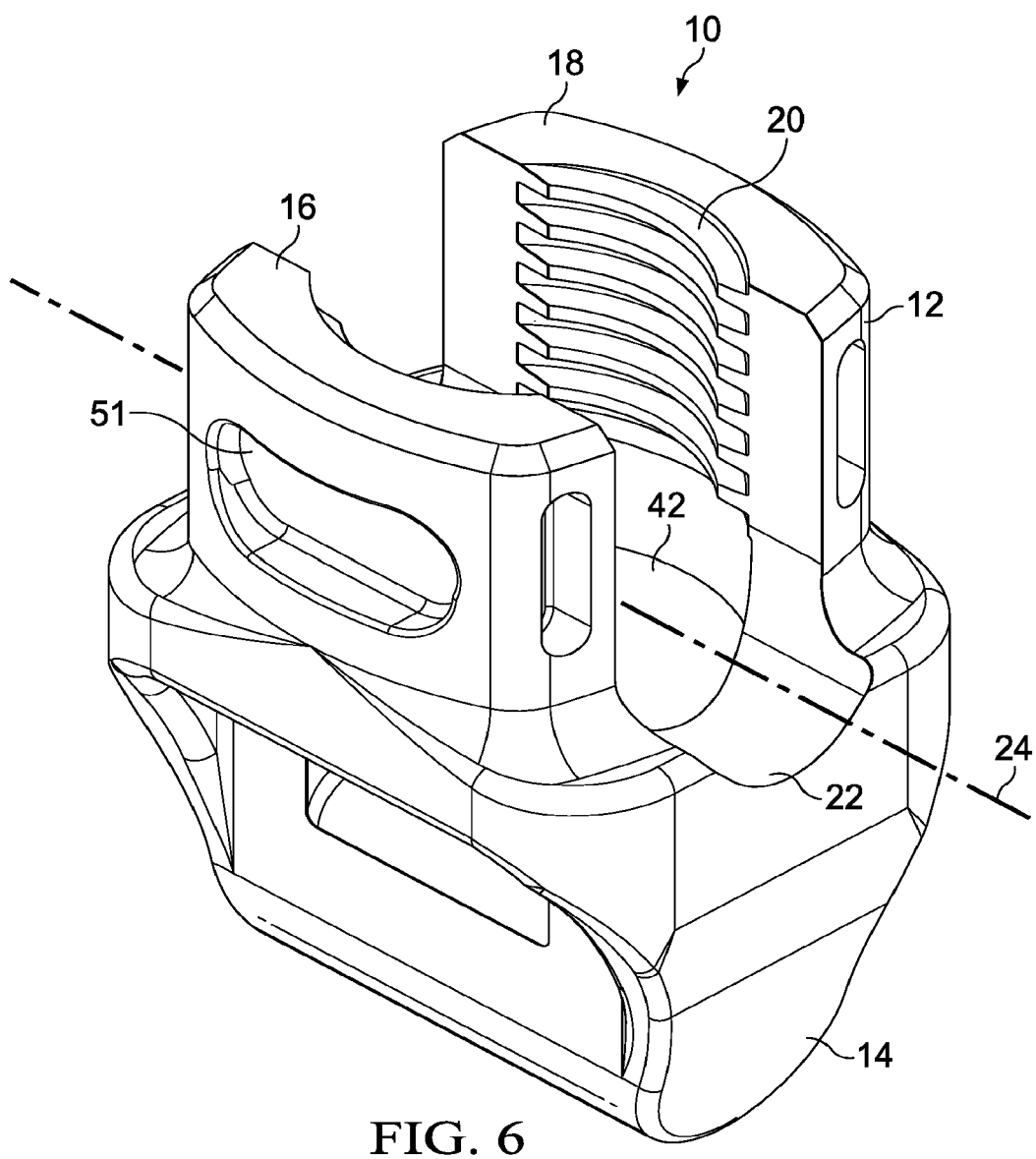
FIG. 6 depicts a perspective view of one example of a pedicle screw extender of the present disclosure.
Figure 7:
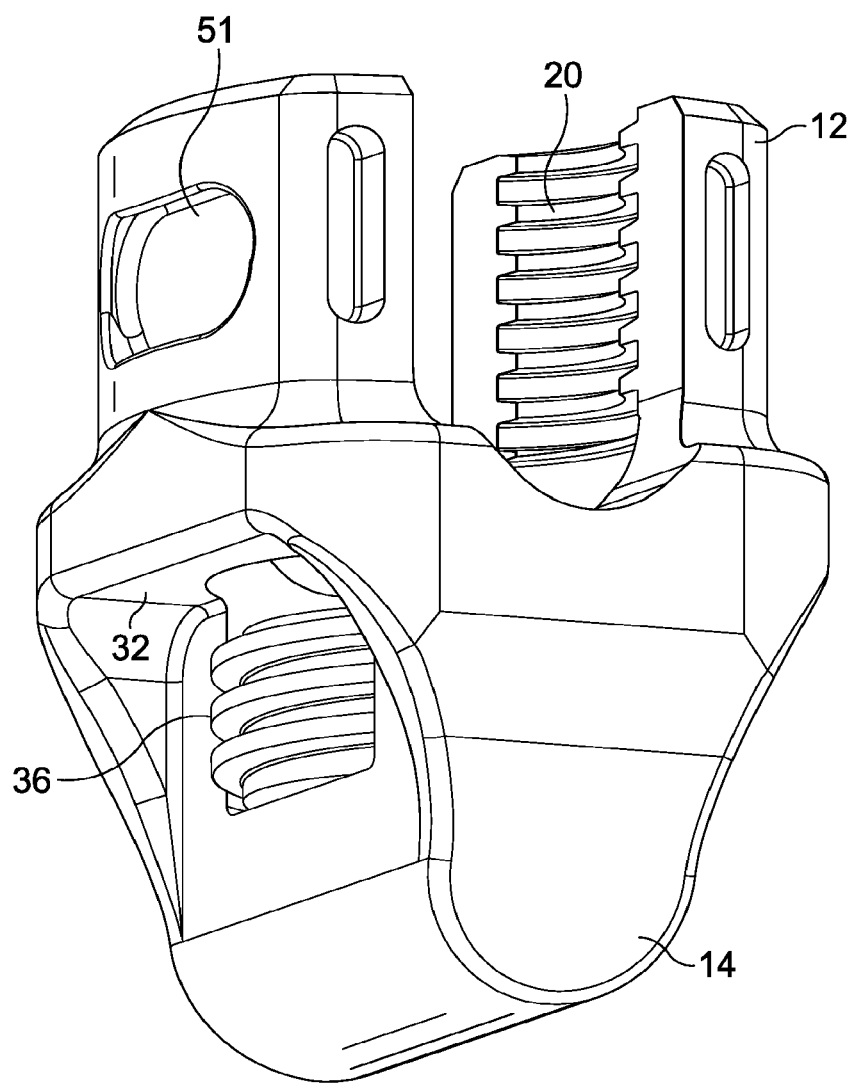
FIG. 7 depicts a perspective view of the pedicle screw extender of FIG. 6.
Figure 8:
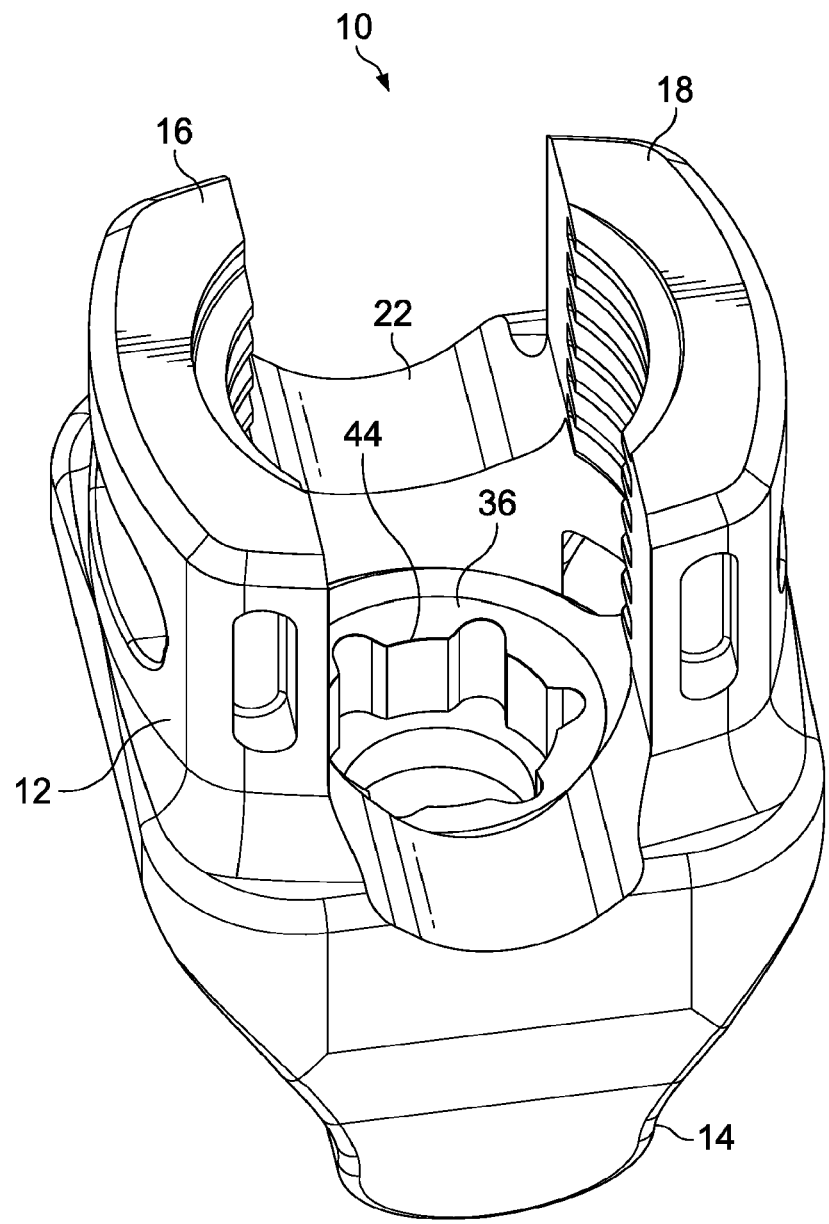
FIG. 8 depicts a top perspective view of the pedicle screw extender of FIG. 6.

An embodiment of tulip head extender 10 similar to that shown in FIG. 4 is depicted in more detail in FIG. 6-12. FIG. 6 illustrates in a perspective view that extender 10 can comprise a one-piece molded body, forged and/or machined body, and, as shown in FIG. 7, a set screw can be disposed internally to the extender 10 body. As an example, extender 10 can be molded of any polymer material, and can be injection molded. As described above, extender 10 can have an upper body portion 12 joined to a lower body portion 14. Upper body portion 12 can have two opposing extender arms 16, 18, each including a portion of interior threads 20. First arm 16 and second arm 18 can extend from a curved lower surface defining a substantially U-shaped interior channel 22 that can have a first channel axis 24. The first channel axis 24 can correspond to, and be coincident with, a longitudinal axis of a rod 122 when reduced into extender 10 (not shown). The first interior threads 20 of first and second arms can be complementary to receive an appropriately sized set screw 36, as shown in FIGS. 7-12. An access opening 42 in upper portion 12 can extend downwardly through the upper portion 12 in a direction generally perpendicular to first channel axis 24. Access opening 42 provides access to the top of extender set screw 36. Extender set screw 36 can have on its top surface a driving portion 44 which can be a male or female socket that can engage with a driver to drive rotation of extender set screw 36. In FIG. 8, a representative female socket driving portion 44 having a generally star-shaped geometry is illustrated.

As can be understood from the description above, first and second extender arms 16 and 18, first interior threads 20, and interior channel 22 correspond to the same or similar functional features of a tulip head, such as tulip head 106 of pedicle screw 100. As can be further understood, the features of the upper portion 12 of extender 10 can include any features 51 desired or required on illustrative bone anchors such as, for example, pockets, tabs, indentations, and openings, to engage with a variety of instruments such as, for example, a particular rod reducing tool, and, as such, facilitate rod reduction by known techniques, albeit reducing the rod a shorter distance than what would have been required to reduce it to the original rod seat 108.

Figure 9:
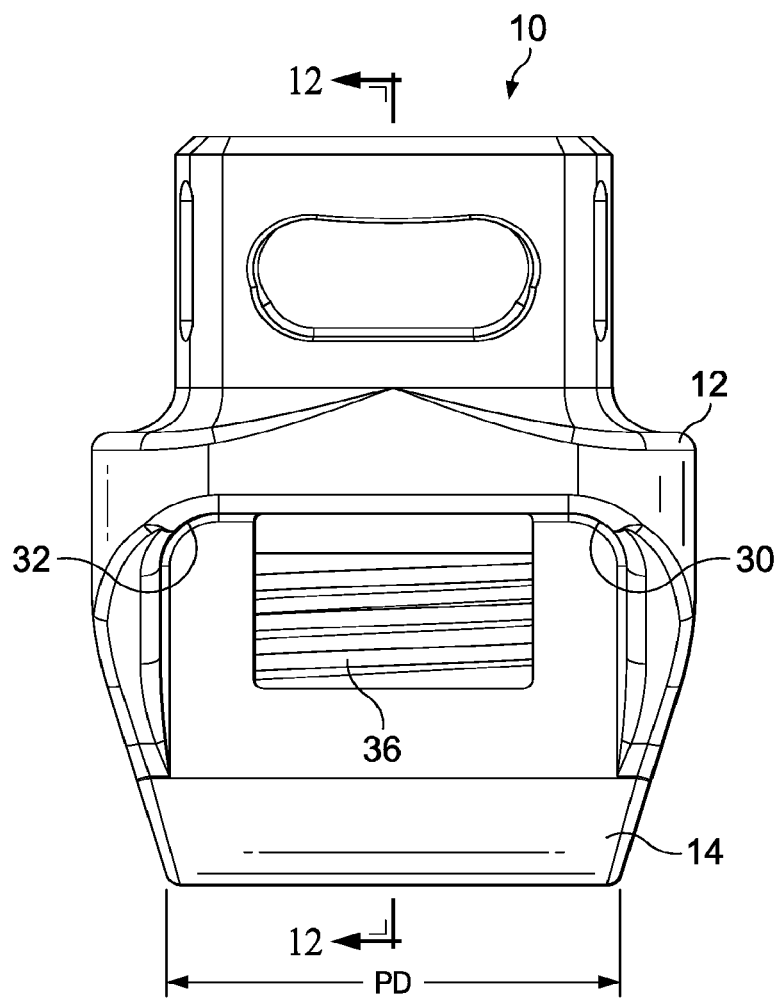
FIG. 9 depicts a side elevation view of the pedicle screw extender of FIG. 6.
Figure 10:
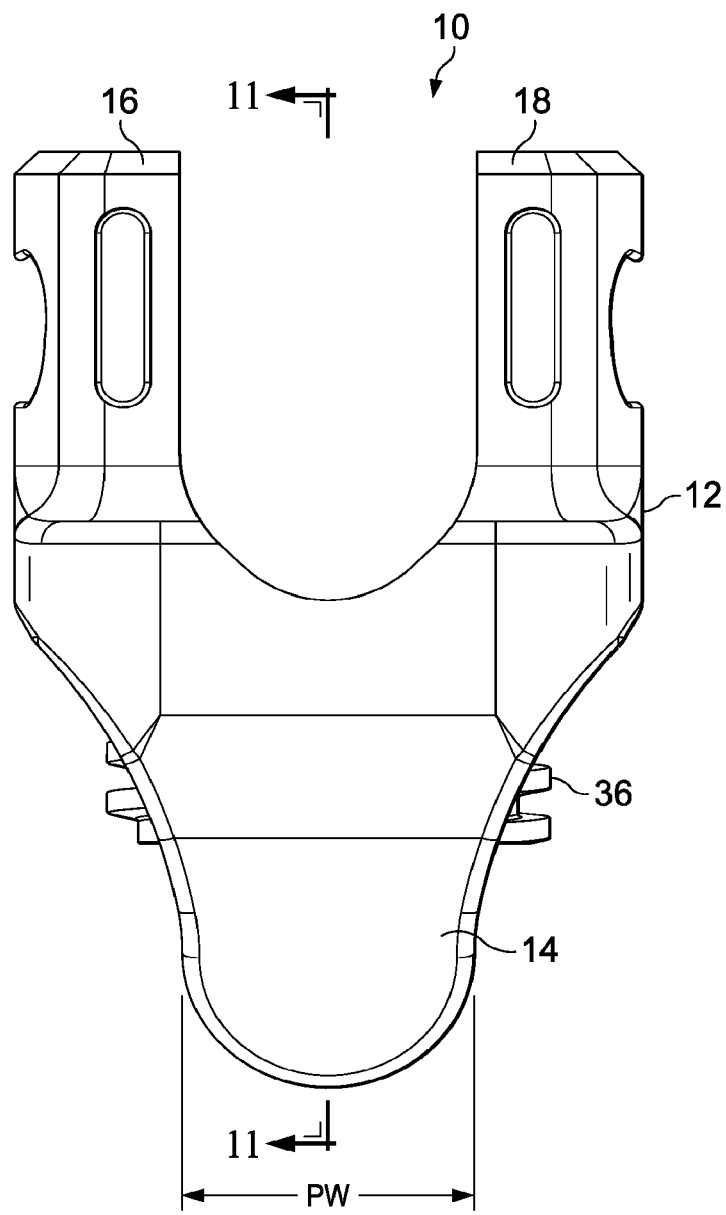
FIG. 10 depicts a side elevation view of the pedicle screw extender of FIG. 6.

As shown in the side elevation views of FIGS. 9 and 10, lower portion 14 can extend downwardly from the upper portion 12, and can have a portion sized to fit into the channel 107 and seat on the rod surface 108 of tulip head 106 of pedicle screw 100. First and second U-shaped sides can be substantially identical in size and shape and have a protrusion width PW having a dimension sized according to the channel width of the tulip head 106 of the pedicle screw 100. First and second U-shaped sides can be spaced apart a distance defining a protrusion depth PD, the protrusion depth PD being a dimension suitable for stable securement to the tulip head 106 of pedicle screw 100, and can be predetermined based on the sizing and requirements of related instrumentation. First and second sides 26 and 28 need not be U-shaped, but can have any shape constrained only in that the lower portion 14 be able to be insertable into and seat with the tulip head 106 of a pedicle screw 100. Thus, first and second sides 26 and 28 can have rectangular shape, for example, and remain functionally capable of being seated into the tulip head 106 of pedicle screw 100.

The extender 10 can have first and second surfaces 30 and 32, which can be generally horizontally oriented portions of the lower surface of upper portion 12, and which can abut the top surface of tulip head 106 of pedicle screw 100 when the extender 10 is set into place. First and second sides 26 and 28 can extend a distance L1 below and generally perpendicular to first and second surfaces 30 and 32 to the bottom of the U-shaped sides. As discussed above with respect to FIG. 5, but for conciseness not shown in FIGS. 9-12, a distance L1 can be substantially equal to the depth of the channel having the rod seat 108 of tulip head 106. Curved lower surface 22 of upper portion 12 of extender 10 can be a distance L2 measured from the bottom of the U-shaped first and second sides 26 and 28. Distance L2 can be greater than distance L1, and can be predetermined by design of extender 10 based on the desired distance D3, as shown in FIG. 4.

Lower portion 14 can have an open interior portion 34 defined between first and second U-shaped sides 26 and 28, and in which can be disposed an extender set screw 36. Open interior portion 34 can have open access through a pair of opposing windows 38, 40 (window 40 on the side not seen in FIG. 5) through which the extender set screw 36 may be inserted into and then, when in its position therein, threads of extender set screw 36 can extend radially outwardly from the windows 38, 40. That is, the outside thread diameter of set screw 36 can be greater than the protrusion width PW. This allows the threads of the extender set screw 36 to threadingly engage the inner threads 116 of the first and second tulip arms 112 when the lower portion 14 is inserted into the tulip channel 107, engaging and/or connecting the extender 10 to the tulip head 100. As can be understood from the description herein, extender set screw 36 serves functionally as the set screw 124 shown in FIG. 3 to set, however, the extender 10 into the tulip head 106 of pedicle screw 100 as shown in FIG. 4 rather than to set the rod 122 into the tulip head as shown in FIG. 3.

Figure 11:
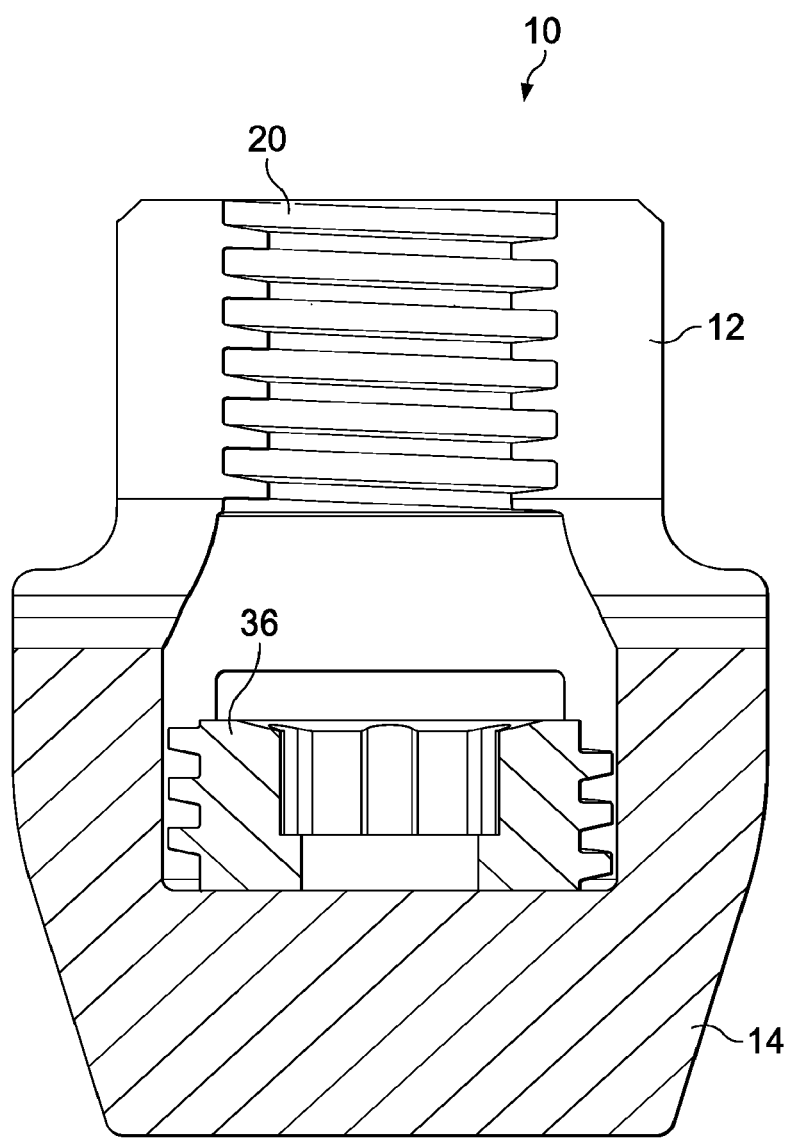
FIG. 11 depicts a partial cross-sectional view of Section 11-11 of FIG. 9.
Figure 12:
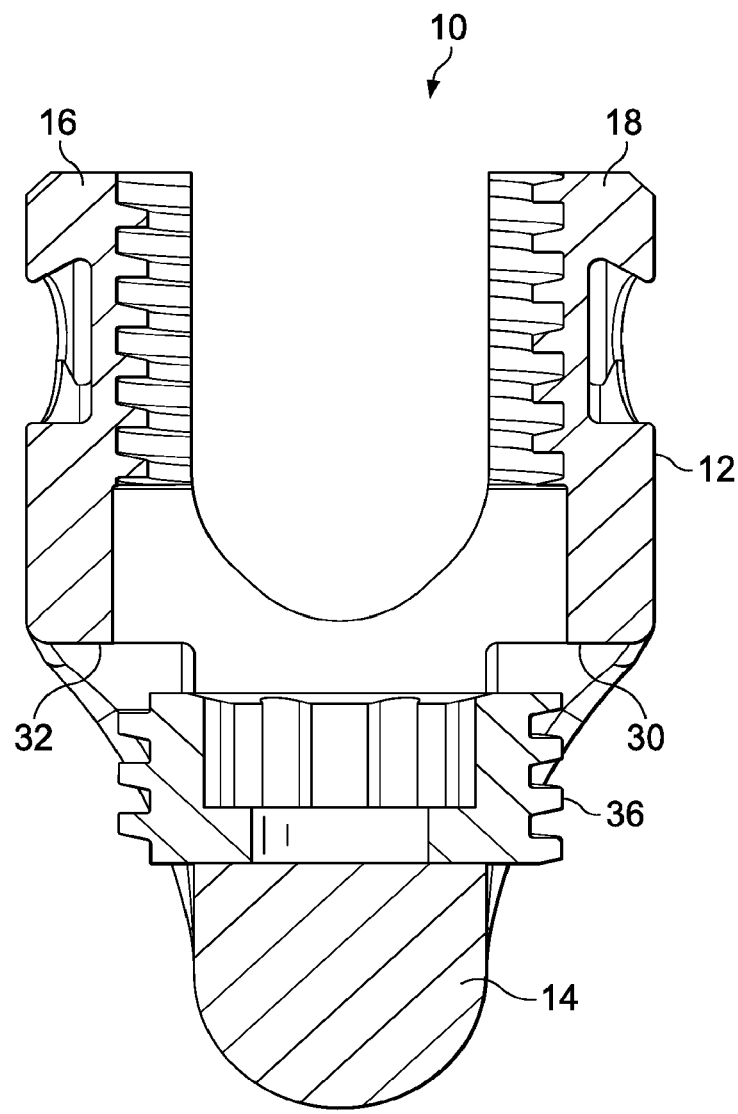
FIG. 12 depicts a partial cross-sectional view of Section 12-12 of FIG. 10.

FIGS. 11 and 12 are partial cross-sectional views of FIGS. 9 and 10 respectively and are provided for descriptive detail with respect to the various structure and features described above. For conciseness all the descriptive detail is not repeated, but the FIGS. can be understood by the description above and the various numbered call-outs of FIGS. 11 and 12.

Figure 13:
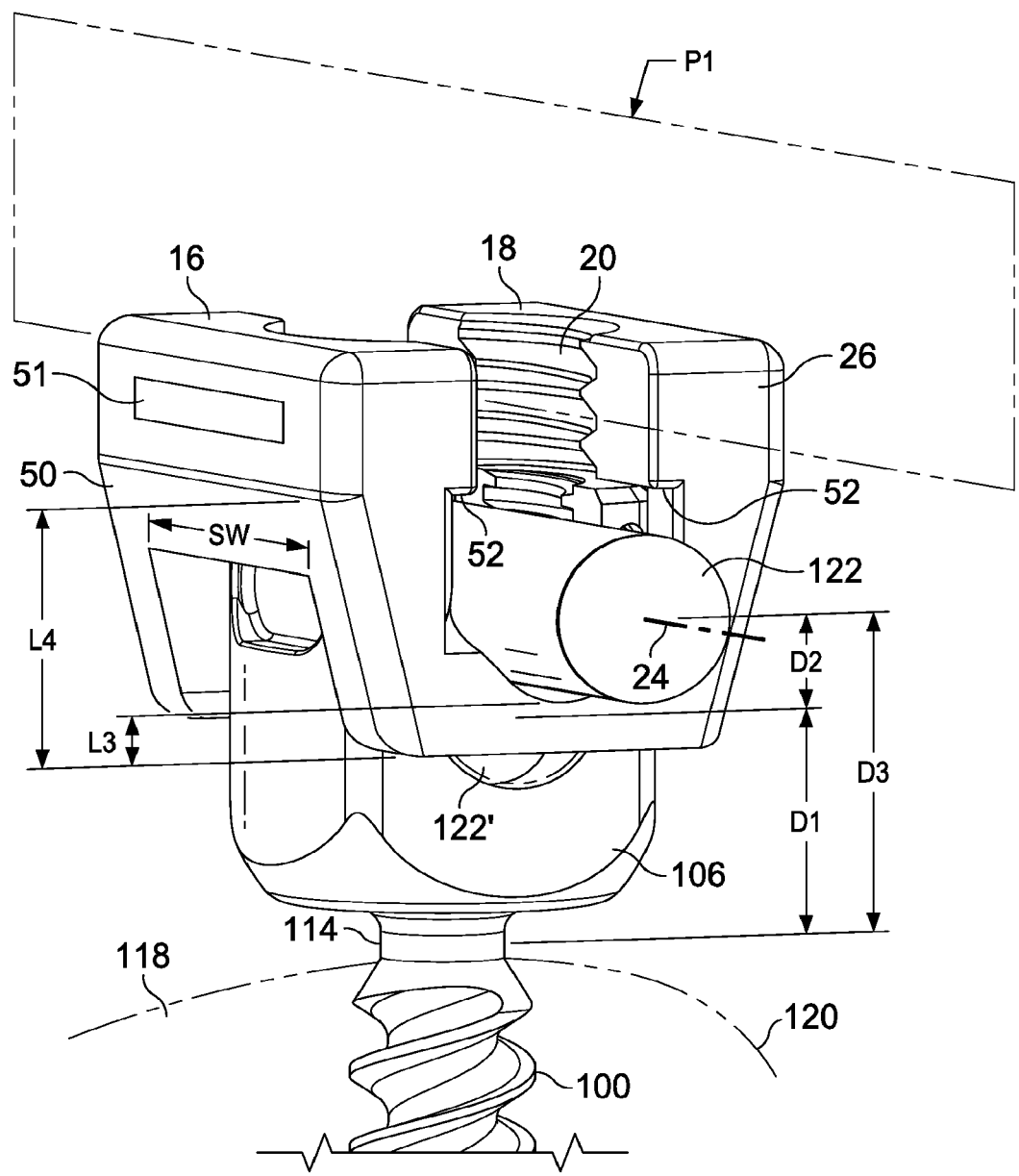
FIG. 13 depicts a perspective view of one example of a pedicle screw extender of the present disclosure.

Referring now to FIG. 13 there is shown another example embodiment of a tulip head extender 10 that, when installed onto tulip head 106, can facilitate the repositioning of rod 122 with respect to bone surface 120 from a distance having a dimension D1 to an additional distance having a dimension D2, for a total distance having a dimension D3. As can be understood, extender 10 permits the vertical repositioning of rod 122 from an original position shown as 122 without disturbing the original position of pedicle screw 100. The dimension D2 can be predetermined by varying the geometry of extender 10, as will be more fully understood in light of the description below.

The example embodiment of extender 10 shown in FIG. 13 can have a rod securing body portion 50 having two opposing arms 16, 18, each including a portion of first interior threads 20. First and second opposing arms can extend upwardly from a curved lower surface defining a substantially U-shaped interior channel 22 that can have a first channel axis 24. First arm 16 and second arm 18 can be described as being opposed across a first imaginary plane P1 parallel to first channel axis 24 and bisecting the securing body portion 50, and, when in use also bisecting tulip head 106 in a like manner.

Extender 10 can have generally parallel spaced apart first and second U-shaped sides, 26 and 28. First and second U-shaped sides can be substantially identical in size and shape and have a separation width SW having a dimension sized according to the size of the tulip head 106 of the pedicle screw 100 over which extender 10 can be lowered and set, somewhat in saddle fashion. First and second sides 26 and 28 (opposite side of side 26) can each have an externally facing surface that is generally planar and perpendicular to the imaginary plane P1. First and second sides 26 and 28 need not be U-shaped, but can have any shape constrained only by general design and function considerations. Thus, first and second sides 26 and 28 can have rectangular shape, for example, and remain functionally capable of being saddled over the tulip head 106 of pedicle screw 100.

The first interior threads 20 of first and second arms can be complementary to receive an appropriately sized set screw (not shown). As can be understood from the description above, first and second arms 16 and 18, first interior threads 20, and interior channel 22 correspond to the same or similar functional features of a tulip head, such as tulip head 106 of pedicle screw 100. As can be further understood, the features of the rod securing body 50 of extender 10 can include any features 51 desired or required on illustrative bone anchors such as, for example, pockets, tabs, indentations, and openings, to engage with a variety of instruments such as, for example, a particular rod reducing tool, and, as such, facilitate rod reduction as known, albeit reducing the rod a shorter distance than what would have been required to reduce it to the original rod seat as shown in FIG. 13.

Rod securing body 50 can be secured to tulip head 106 in any suitable manner, for example, by securing to mating engagement portions. For example, rod securing body 50 can have tabs that can engage pockets 114 of tulip head 106. In an embodiment, tabs of rod securing body can be flexibly resilient, and can be separated apart while rod securing body is pressed down onto tulip head 106 and snapped inwardly when tabs engage pockets 114. In another embodiment, a first set screw can be, optionally, threadingly engaged to the internal extender threads 20 and threaded through the extender until it threadingly engages the internal threads 116 of tulip head 106. The first set screw can be threaded into the tulip head to the desired position to secure and/or hold a spinal fixation rod 122 in position within the extender channel between the curved surface of the channel 22 and the first set screw, and at the same time, to hold and/or secure the extender 50 to tulip head 106. Optionally, a second extender set screw (e.g., extender set screw 36) can be threadingly engaged to the internal threads 20 of the extender 50 to provided additional hold and/or securement of the spinal fixation rod 122 to the extender. Rod securing body 50 can have generally flat, inwardly extending surfaces 52 that can abut the top surface of tulip head 106 when rod securing body is positioned for receiving a rod. Interior channel 22 can have a lower surface a distance having a dimension L3 above the lower surface of the extender 10. Inwardly extending surfaces 52 can be disposed at a forth distance having a dimension L4 above the lower surface of extender 10.

Once extender 10, as described with reference to FIG. 13, is secured to tulip head 106 by placing over the tulip head 106 in a saddle-like fashion, first and second arms 16 and 18, first interior threads 20, and interior channel 22 effectively define a second tulip head into which a rod 122 can be reduced. The dimension D2 above which a rod would be reduced into tulip head 106 of pedicle screw 100 can be predetermined by adjusting by design the various described components and dimensions. Thus, in operation, a doctor or other operator can choose an extender 10 having dimensions, including dimensions L3 and L4 for the particular pedicle screw 100 being utilized, and the desired dimension D3 for elevated rod reduction. As can be understood, therefore, extender 10 provides great flexibility to increase the rod reduction height relative to bone surface 120 for a fixed position of a tulip head 106 of a fixed pedicle screw 100.

Thus, according to the description above with reference to FIG. 13, it can be understood that in an embodiment extender 10 can be attached to the tulip head 106 of a pedicle screw 100 to increase the distance from bone surface 120 from a first distance having a dimension D1 to a third distance having a dimension D3, which is greater than D1. Once extender 10 is secured to tulip head 106, first and second arms 16 and 18, first interior threads 20, and interior channel 22 effectively define a second tulip head into which a rod 122 can be reduced. The second dimension D2 above which a rod would be reduced into tulip head 106 of pedicle screw 100 can be predetermined by adjusting by design the various described components and dimensions. Thus, in operation, a doctor or other operator, can choose an extender 10 having dimensions, including dimensions L3 and L4 for the particular pedicle screw 100 being utilized, and the desired dimension D3 for rod reduction. As can be understood, therefore, extender 10 provides great flexibility to increase the rod reduction height relative to bone surface 120 for a fixed position of a tulip head 106 of a fixed pedicle screw 100.

Figure 16:
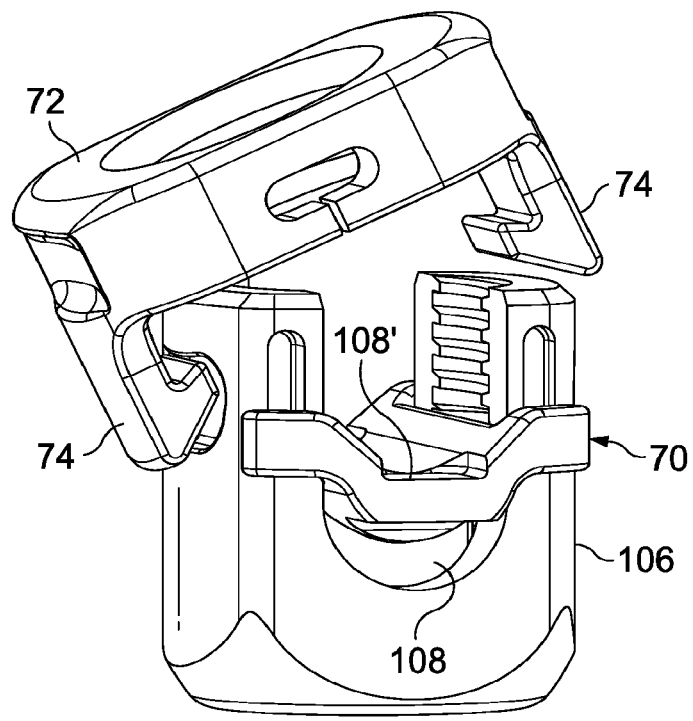
FIG. 16 depicts a perspective view of the pedicle screw extender of FIG. 14 partially engaged with a head of a pedicle screw.
Figure 17:
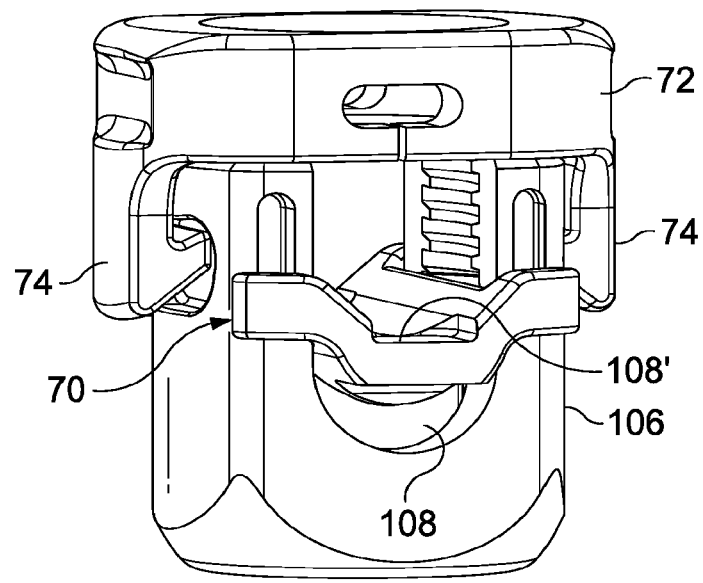
FIG. 17 depicts a perspective view of a portion of the pedicle screw extender of FIG. 14 engaged with a head of a pedicle screw.
Figure 18:
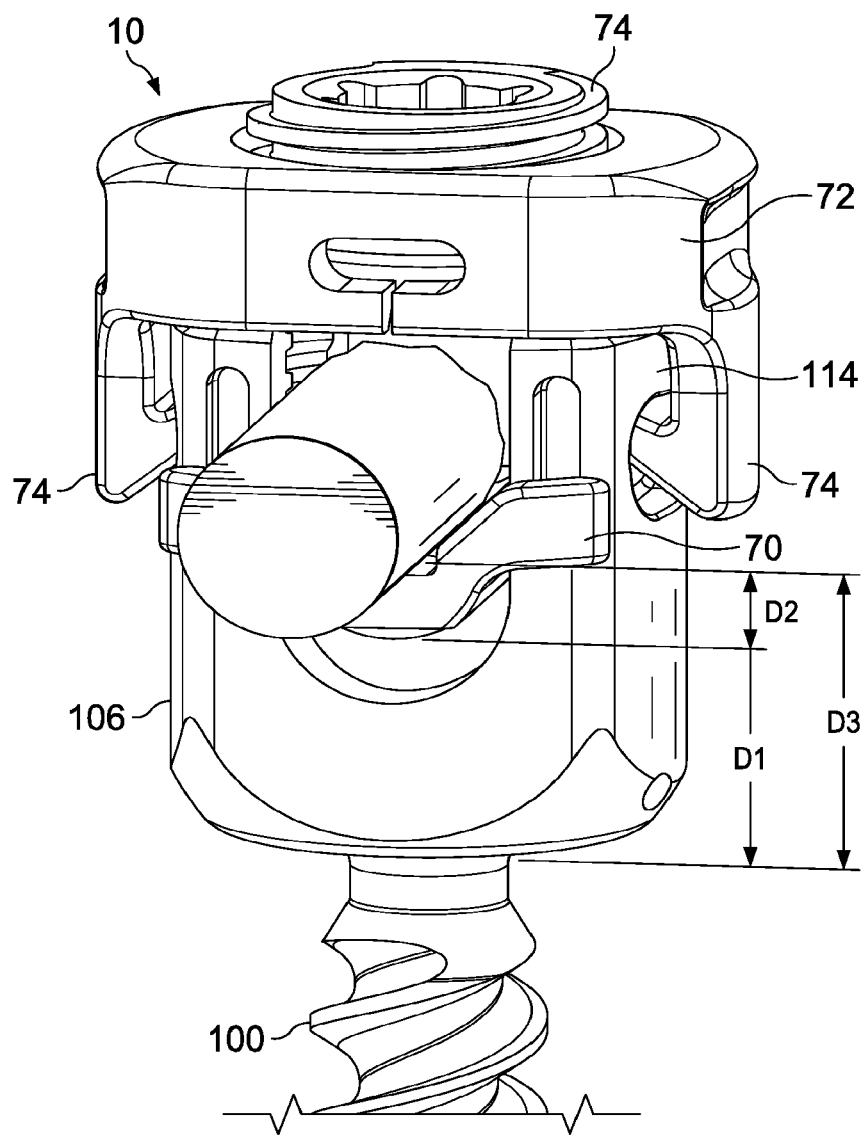
FIG. 18 depicts a schematic perspective view of the pedicle screw extender of FIG. 14 engaged with a head of a pedicle screw.

Referring now to FIGS. 14-21, there is shown another example embodiment of a tulip head extender 10 that, when installed onto tulip head 106, can facilitate the repositioning of rod 122 with respect to bone surface 120 from a distance having a dimension D1 to an additional distance having a dimension D2, for a total distance having a dimension D3 (as depicted in FIG. 18). As can be understood by the description herein, extender 10 permits the vertical repositioning of rod 122 without disturbing the original position of a pedicle screw 100. The dimension D2 can be predetermined by varying the geometry of extender 10, as will be more fully understood in light of the description below.

Figure 14:
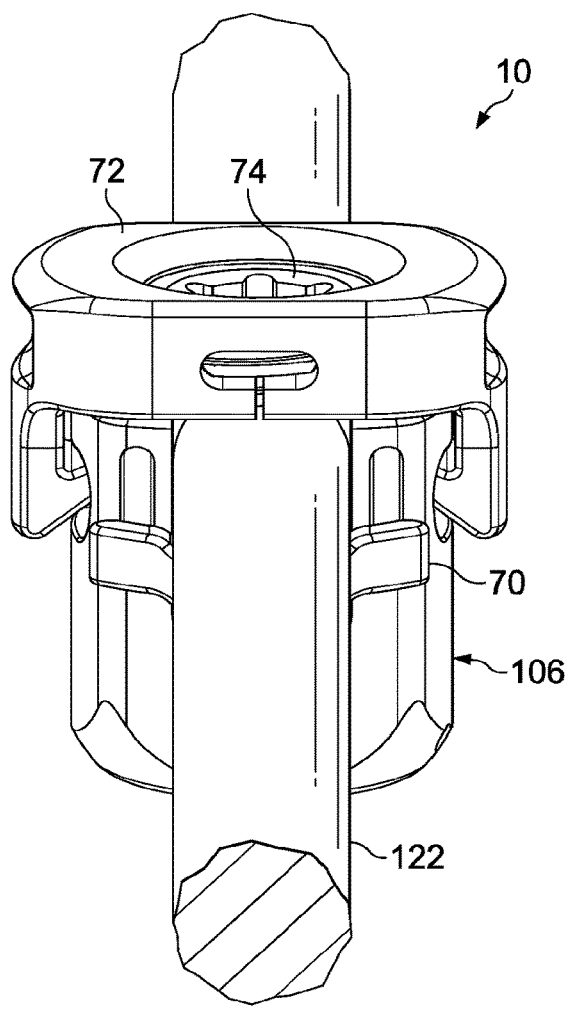
FIG. 14 depicts a perspective view of one example of a pedicle screw extender of the present disclosure engaged to head of a pedicle screw.

As shown in the embodiment of FIGS. 14-21, extender 10 can comprise three discrete parts that together serve to fix a spinal fixation rod 122 on a pedicle screw head 106 at an elevated distance from the bone in which pedicle screw is affixed. FIG. 14 shows a perspective view of an extender 10 comprising three discrete parts, namely a saddle 70, a cap 72, and a set screw 74, which can be in all respects identical to the set screw 36 described above. All three parts can be made of any suitable material, including injection molded polymer materials.

Figure 15:
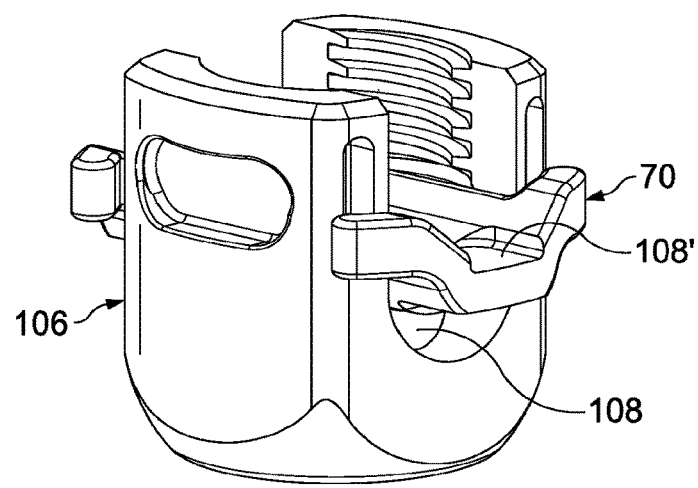
FIG. 15 depicts a perspective view of a portion of the pedicle screw extender of FIG. 14.

Referring to FIG. 15, saddle 70 can be disposed within the tulip head 106 of a pedicle screw (i.e., within channel 107). Saddle 70 can be slid into the tulip head 106 and can rest on the rod seat 108. Saddle 70 can have on the upper, rod-facing side a surface that defines an elevated rod seat 108. Saddle 70 is described in more detail with respect to FIG. 19.

Referring to FIG. 16, a cap 72 can be snapped onto tulip head 106, for example, by utilizing tabs 74 that can clip onto pockets 114 of tulip head 106. One tab 74 can be hooked into one pocket 114, and the cap 72 can be rotated and pressed such that the other tab 74 can be hooked, or snapped, into the opposite pocket 114. In other words, the tabs 74 can be fabricated from a material and/or by design such that one or more of the tabs 74 can flex outward to go over and/or about the outer circumference of the tulip head and then snap back into its normal position into one or more of the pockets 114. Once snapped onto tulip head 106, cap 72 is secured onto tulip head 106 as shown in FIG. 17. A spinal fixation rod 122 may be positioned into the saddle prior to the cap 73 being positioned upon and secured to the tulip head, thus positioning the rod 122 between the saddle and the cap. Once positioned, the set screw 36 may be threadingly engaged to the tulip head 106 and/or the cap 72. Alternatively, once the saddle 70 and cap 72 are positioned onto the tulip head 106, a spinal fixation rod 122 can be positioned between them, and secured to the tulip head 106 by inserting and securing a set screw 36, as shown in FIG. 14 (i.e., threadingly engaged to the tulip head 106 and/or the cap 72).

A schematic perspective view of the extender 10 shown in FIGS. 14-17 is depicted in FIG. 18. Once extender 10, as described with reference to FIGS. 14-16, is secured to a pedicle screw head 106 having a rod seat 108 at an elevation D1 above the bone surface, the elevated rod seat 108' can be elevated above the rod seat 108 by a distance having a dimension D2 which can be predetermined by adjusting by design the various described components and dimensions. Thus, in operation, a doctor or other operator can choose an saddle 70 having dimensions, specifically a saddle height dimension as discussed below, for the particular pedicle screw 100 being utilized, and the desired dimension D3 for elevated rod reduction. As can be understood, therefore, extender 10 provides great flexibility to increase the rod reduction height relative to bone surface 120 for a fixed position of a tulip head 106 of a fixed pedicle screw 100.

Figure 19:
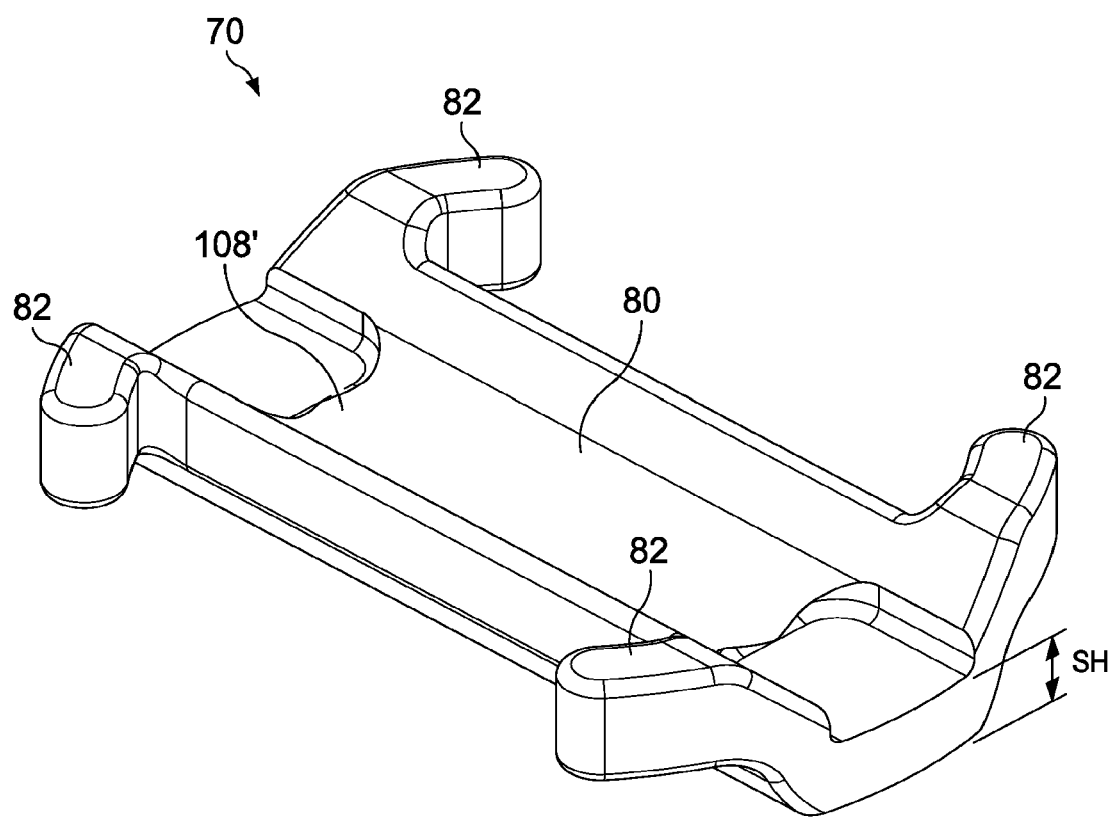
FIG. 19 depicts a perspective view of a portion of the pedicle screw extender of FIG. 14.

FIG. 19 shows a perspective view of a representative saddle 70 used in the extender 10 shown in FIGS. 14-17. In particular, saddle 70 can be generally H-shaped having a longitudinally extending curved surface 80 that serves as the elevated rod seat 108. A pair of opposing guide tabs 82 can be disposed at each longitudinal end of the curved surface 80. The size and spacing of tabs 82 can be predetermined according to the dimensions of the tulip head 106 onto which saddle 70 is placed. Saddle 70 can have a thickness from a bottom surface to a top surface of the elevated rod seat 108' SH, as shown in FIG. 19. The saddle height SH can be predetermined for the desired dimension D3 for elevated rod reduction.

Figure 20:
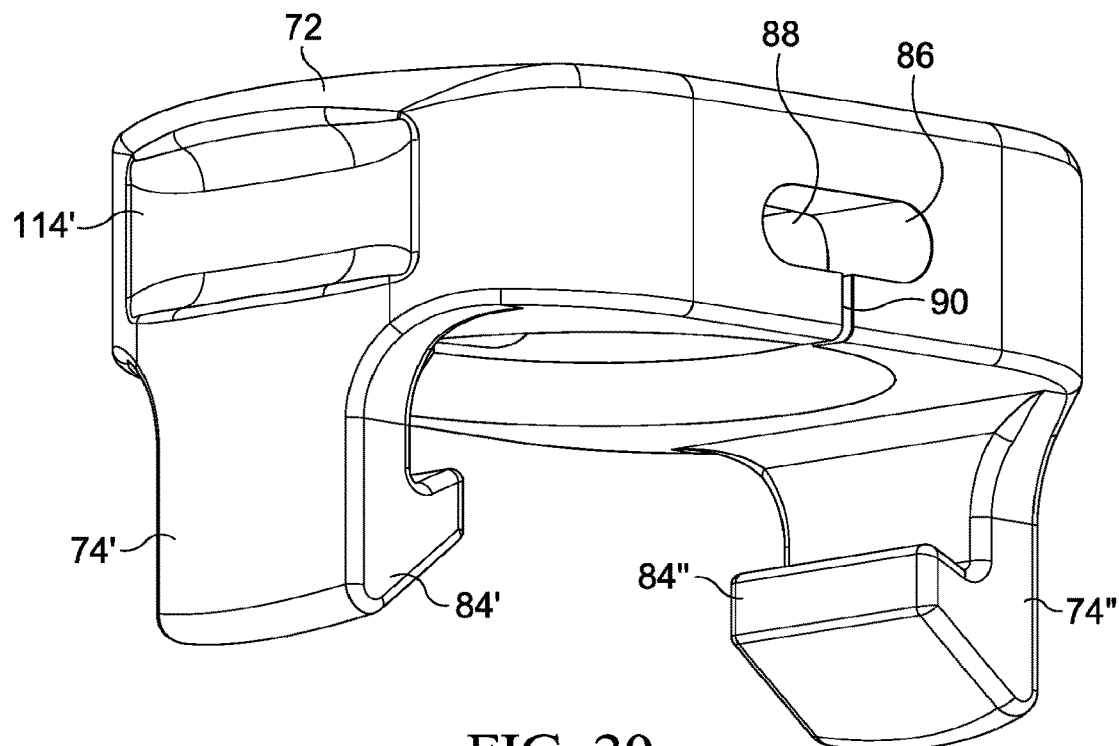
FIG. 20 depicts a perspective view of a portion of the pedicle screw extender of FIG. 14.

Referring to FIG. 20, there is shown a perspective view of cap 72. Cap 72 can have two opposed tabs 74 that can have a general hook-shape such that a first tab 74' with a hook feature 84' that can engage with a pocket 114 of tulip head 106, as illustrated above with respect to FIG. 16. A second tab 74" with a second hook feature 84" can be pressed down and snapped into a pocket 114 on the opposite side of a tulip head 106. A stress relief feature 86, which can include a slot 88 and/or a slit 90 on the upper portion of cap 72, from which tabs 74 extend downwardly, can be included on cap 72. Cap 72 can also have indented features, such as a pocket 114' on opposite side surfaces of cap 72. Pockets 114' provide a connection for connectivity and operation of known instruments such as, for example, a driving tool and/or rod reducing tool.

Figure 21:
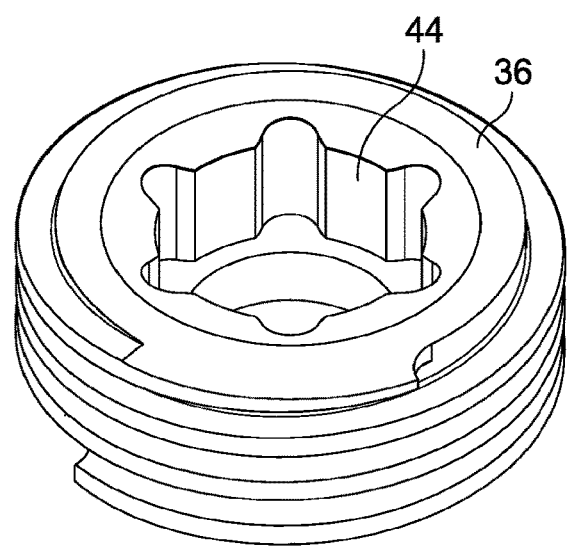
FIG. 21 depicts a perspective view of a portion of the pedicle screw extender of FIG. 14.

Referring to FIG. 21 there is illustrated in perspective a set screw 36 having external threads that engage with the internal threads of the tulip head of a pedicle screw, or other internal threads of extenders 10 as described herein. Set screw 36 can be turned by a tool that can be inserted into a driving portion 44 that can be a socket into which a driving tool can be inserted and securely rotated to rotate set screw 36.

Figure 22:
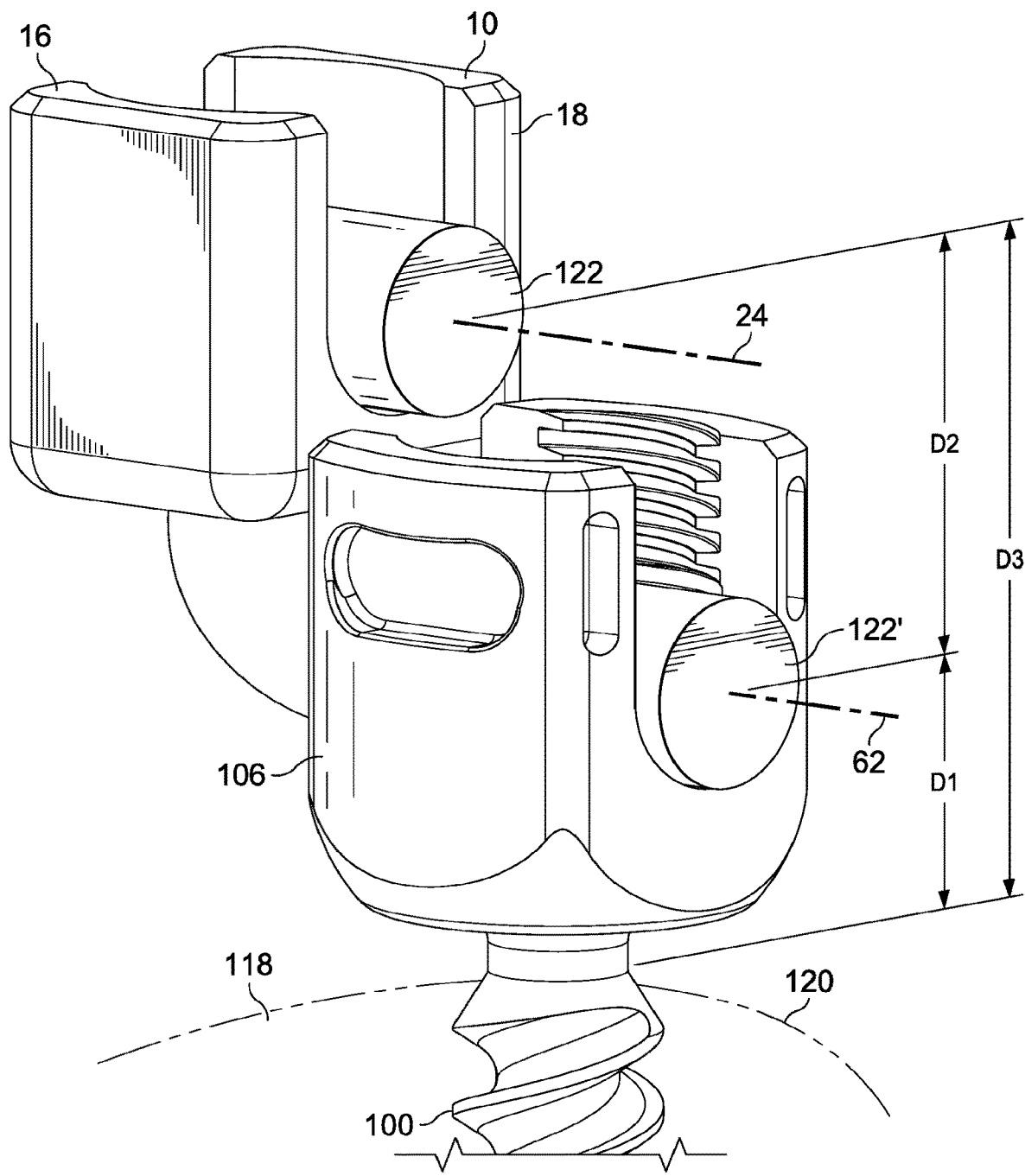
FIG. 22 depicts a perspective view of one example of a pedicle screw extender of the present disclosure.
Figure 23:
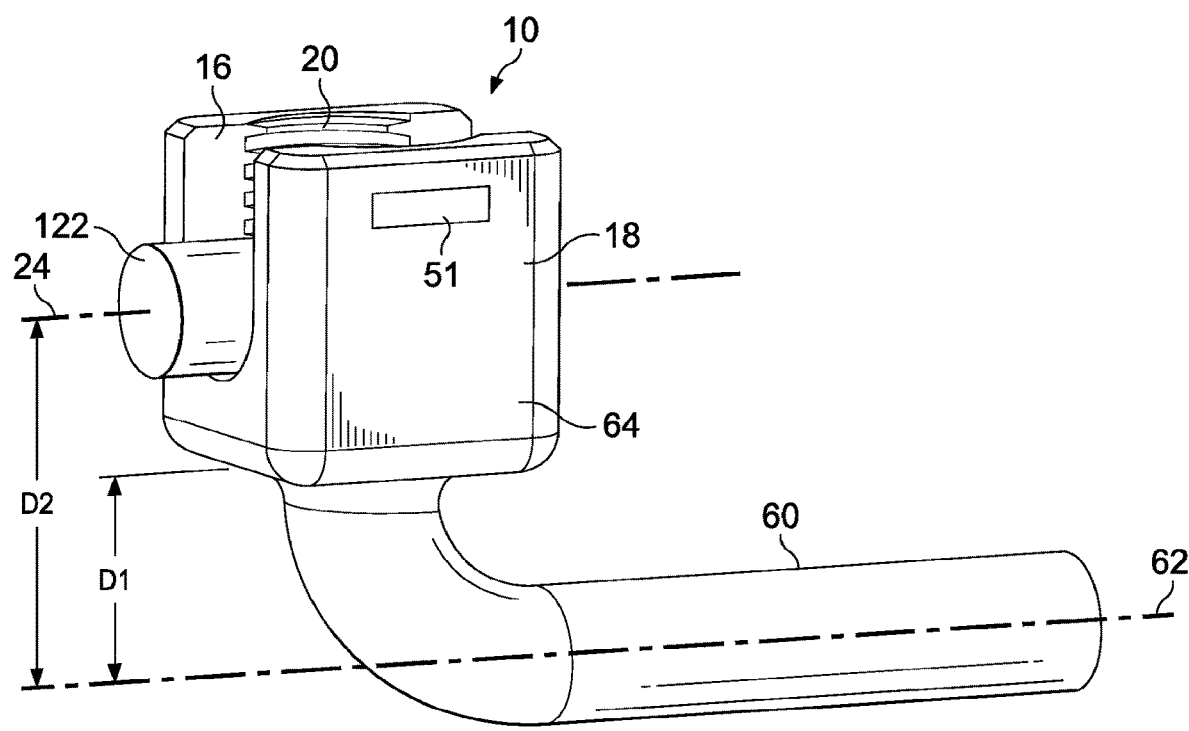
FIG. 23 depicts a perspective view of one example of a pedicle screw extender of the present disclosure.
Figure 24:
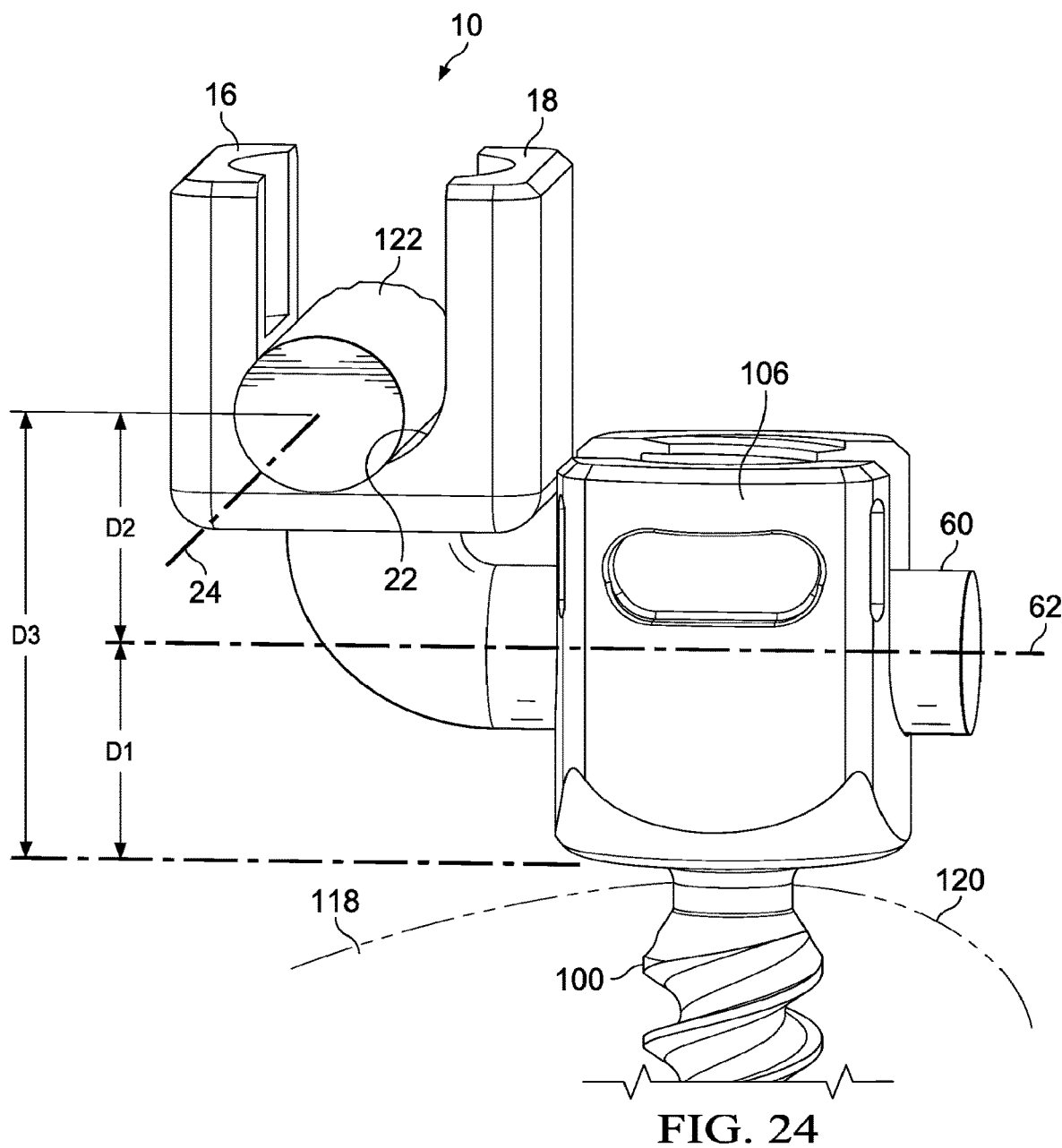
FIG. 24 depicts a perspective view of one example of a pedicle screw extender of the present disclosure.
Figure 25:
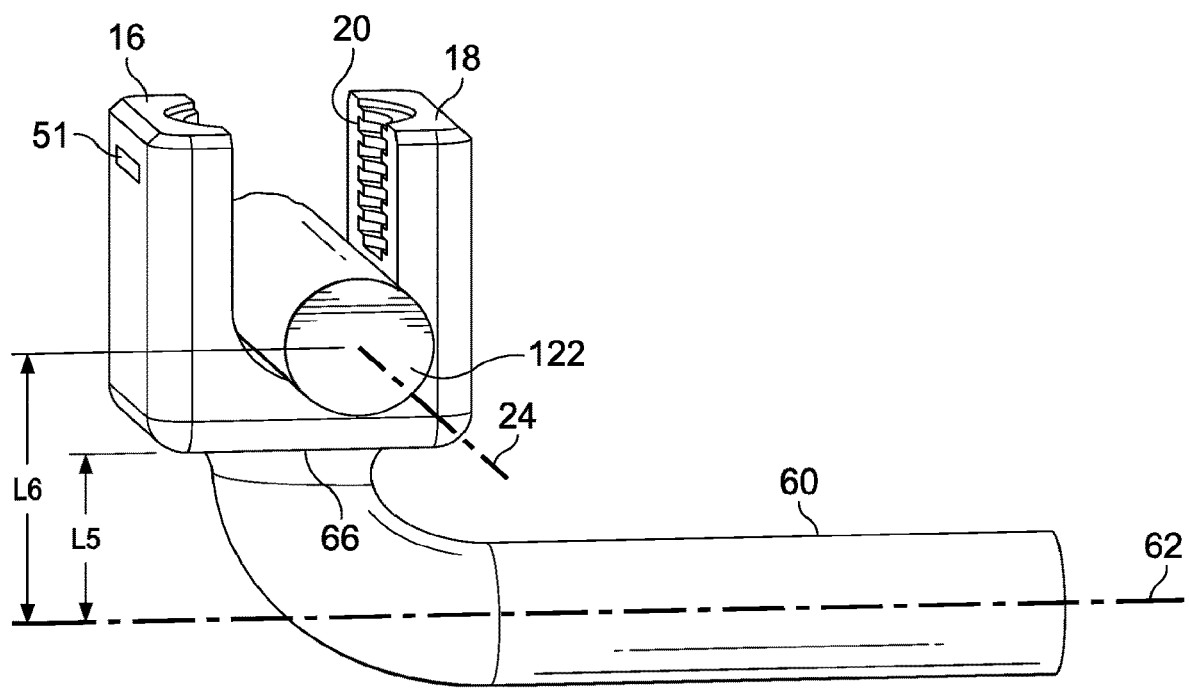
FIG. 25 depicts a perspective view of one example of a pedicle screw extender of the present disclosure.

Referring to FIGS. 22-25 there is illustrated further example embodiments of extenders 10 that facilitate positioning of a spinal fixation rod 122 both laterally and upwardly with respect to a fixed pedicle screw 100 tulip head 106. FIGS. 22 and 23 illustrate an extender 10 that facilitates laterally elevated in-line positioning of rod 22. FIGS. 24 and 25 illustrate an extender 10 that facilitates laterally elevated cross positioning of rod 22.

As shown in FIG. 22, an extender 10 is illustrated that permits a rod 122 to be reduced to an elevation greater than the elevation dictated by a pedicle screw 100 fixed in a bone 118. As shown in FIGS. 22 and 23, extender 10 can be a unitary construction, and can have a mounting bar 60 that can be cylindrical, and can be sized to fit and be secured into tulip head 106 of fixed pedicle screw 100. Securement of mounting bar 60 into tulip head 106 can be, for example, by a set screw (not shown) tightened into internal threads 116 of tulip head 106. Mounting bar can have any cross section, but can be a cylindrical shape having a central axis 62.

Extender 10 as illustrated in FIGS. 22 and 23 can have disposed on an upturned end of mounting bar 60 an extender tulip head 64 that can be in size, shape, and function, substantially identical to tulip head 106 of pedicle screw 100. In general, extender tulip head 64 can have two opposing arms 16, 18, each including a portion of interior threads 20. First arm 16 and second arm 18 can extend from a curved lower surface defining a substantially U-shaped interior channel 22 that can have a first channel axis 24 can be coincident with the central axis of rod 122 and can be generally parallel to and in the same plane as central axis 62. The first interior threads 20 of first and second arms can be complementary to receive an appropriately sized set screw (not shown). As can be understood from the description herein, first and second arms 16 and 18, first interior threads 20, and interior channel 22 correspond to the functional features of a tulip head, such as tulip head 106 of pedicle screw 100. As can be further understood, the features of the extender tulip head 64 can include any features required (but not shown) to engage with a particular rod reducing tool, and, as such, facilitate rod reduction as known, albeit reducing the rod to distance having a dimension D3 rather than distance a lesser dimension D1, as shown in FIG. 22.

In the embodiment illustrated in FIGS. 22 and 23, the first channel axis 24 and the central rod axis 62 of mounting bar 60 are parallel and in the same plane, and thus a fixation rod 122 reduced into extender tulip head 64 is "in line" with the mounting bar 60, and thus in line directionally with where the fixation rod 122 would have been mounted in the tulip head 106 of pedicle screw 100.

As can be understood with respect to FIGS. 24 and 25, an example of another extender 10 that facilitates fixation of a rod 122 both laterally and upwardly with respect to a fixed pedicle screw 100 tulip head 106 is shown. The extender of FIGS. 24 and 25 is identical in most respects to that shown in FIGS. 22 and 23, with the material difference being that extender tulip head 64 has a different orientation, such that a rod 122 reduced into it would not be "in line" with mounting bar, but be at some angle to it, albeit remaining elevated by distance having a dimension D2 with respect to the mounting bar. In an embodiment, first arm 16 and second arm 18 can extend from a curved lower surface defining a substantially U-shaped interior channel 22 that can have a first channel axis 24 that is generally parallel to but in different plane than central axis 62. In an embodiment, first channel axis 24 can be in a plane that is substantially perpendicular to a plane in which central axis 62 resides. However, in general, as described above, the first interior threads 20 of first and second arms can be complementary to receive an appropriately sized set screw (not shown). As can be understood from the description herein, first and second arms 16 and 18, first interior threads 20, and interior channel 22 correspond to the functional features of a tulip head, such as tulip head 106 of pedicle screw 100. As can be further understood, the features of the extender tulip head 64 can include any features required (but not shown) to engage with a particular rod reducing tool, and, as such, facilitate rod reduction as known, albeit reducing the rod to distance to a dimension D3 rather than to a distance having a dimension D1 which is less than D3, as shown in FIG. 24.

As depicted in FIG. 25 dimension D3 can be varied depending on the dimensions of extender 10, specifically the distance which can be measured from mounting bar axis 62 and a lower surface 66 of head 64, which distance can be the dimension L5. More particularly, dimension D3 can be varied depending on the distance which can be measured from mounting bar axis 62 and a rod seating surface 22 of head 64, which distance can be the dimension L6.

The extenders 10 disclosed herein can provide a benefit in the installation and use of spinal fixation rods. In general, a method of use of extender 10 includes affixing an extender 10 to an installed tulip head of a pedicle screw, thereby extending, with respect to the pedicle bone, the distance from the pedicle bone that a spinal fixation rod will seat. In general, an extender 10 can safely span a gap between the distance from the pedicle bone of the rod seat 108 of a tulip head 106 of an installed pedicle screw and the distance that is determined as safely seating a spinal fixation rod.

For extenders 10 of the type illustrated and disclosed, for example, with respect to FIGS. 4-12, the extender 10 can have a set screw, e.g., set screw 36 of FIGS. 8 and 10, threaded through the extender 10 and threaded onto the internal threads 116 of the tulip head 106, thereby securing the extender 10 to the tulip head 106. After the extender 10 is secured to the tulip head 106, a spinal fixation rod 122 can be seated in the extender and secured, e.g., with another set screw threaded into first interior threads 20 as depicted in FIG. 5.

For extenders 10 of the type illustrated and disclosed, for example, with respect to FIGS. 14-21, the saddle 70 provides for the extended distance with respect to the pedicle bone, i.e., the distance from the pedicle bone that a spinal fixation rod will seat. The cap 72 can then be snapped over the top of the tulip head into the slots on the side thereof. A set screw can then be tightened down, thereby pulling the cap 72 upward on the slots locking it in place.

The apparatuses and methods disclosed herein may be used and/or applied in any regions of the spine such as for example, cervical, thoracic, lumbar, sacral, or coccygeal regions. In some examples, the apparatuses and methods disclosed herein may be used and/or applied in severely curved regions of the spine, for example, the lumbar region of the spine, i.e., for a spinal fixation rod secured to any or all of L1-L5 vertebrae. The lumbar region can often exhibit extreme lumbar curves where a spinal fixation rod would necessarily need to be significantly deformed, thus creating large stresses in the rod and/or the pedicle screw and/or the bone, as well as possible fracture of either the rod, screw, or bone. Extenders 10 can also be used in other vertebrae, including, for example, in the upper thoracic region for severe kyphosis, i.e., for a spinal fixation rod secured to any or all of T1-T12 vertebrae, where there can also be significantly rod stresses present. Extenders 10 can also be used in vertebrae of the cervical region, i.e., for a spinal fixation rod secured to any or all of C1-C7.

Representative embodiments of the present disclosure described above can be described as follows.

In an embodiment a method of use can include the following steps: inserting a pedicle screw having a tulip head in a vertebral bone to a predetermined distance; placing a spinal fixation rod in close proximity to, e.g., hovering over, the tulip head of the inserted pedicle screw; determining that the distance the spinal fixation rod must be reduced into the tulip head is too great to allow for safe reduction of the spinal fixation rod into the tulip head, e.g., because of the likelihood of excessive stress on the pedicle bone; securing an extender 10 to the tulip head of the pedicle screw; seating the spinal fixation rod into the extender 10; and securing the spinal fixation rod into the extender 10.

A method of use for extenders as described above can be described as a method for securing a spinal fixation rod to a pedicle bone, the method including the following steps: providing a tulip head of a pedicle screw; providing a spinal fixation rod; securing an extender 10 to the tulip head of the pedicle screw; seating the spinal fixation rod into the extender 10; and securing the spinal fixation rod into the extender 10.

A method of use for extenders as described above can be described as a method for securing a spinal fixation rod to a pedicle bone, the method including the following steps: providing a tulip head of a pedicle screw screwed into a pedicle bone; providing a spinal fixation rod; securing an extender 10 to the tulip head of the pedicle screw; seating the spinal fixation rod into the extender 10; and securing the spinal fixation rod into the extender 10.

A method of use for extenders as described above can be described as a method for securing a spinal fixation rod to a pedicle bone, the method including the following steps: providing a plurality of pedicle screws each comprising a tulip head, and each screwed into a respective pedicle bone; securing at least one extender 10 to the tulip head of at least one of the tulip heads of at least one of the pedicle screws; bending a spinal fixation rod to an approximate shape; seating the bent spinal fixation rod into the at least one extender 10; and securing the spinal fixation rod into the at least one extender 10.

A method of use for extenders as described above can be described as a method for securing a spinal fixation rod to a pedicle bone, the method including the following steps: providing a plurality of pedicle screws each comprising a tulip head, and each screwed into a respective pedicle bone; recognizing that the required shape of an attached spinal fixation rod will exert excessive stress on the pedicle bone; securing at least one extender 10 to the tulip head of at least one of the tulip heads of at least one of the plurality of pedicle screws; bending a spinal fixation rod to an approximate shape; seating the bent spinal fixation rod into the at least one extender 10; and securing the spinal fixation rod into the at least one extender 10.

A method of use for extenders as described above can be described as a method for securing a spinal fixation rod to a pedicle bone, the method including the following steps: on the spine of a patient in need of orthopedic surgery, providing a plurality of pedicle screws each comprising a tulip head, and each screwed into a respective pedicle bone of the spine; recognizing that the required shape of an attached spinal fixation rod exerts excessive stress on the pedicle bone; securing at least one extender 10 to at least one of the tulip heads of at least one of the plurality of pedicle screws;

bending a spinal fixation rod to an approximate shape; seating the bent spinal fixation rod into the at least one extender 10; and securing the spinal fixation rod into the at least one extender 10.

A method of use for extenders as described above can be described as a method for securing a spinal fixation rod to a pedicle bone, the method including the following steps: on the lumbar region of a spine of a patient in need of orthopedic surgery, providing a plurality of pedicle screws each comprising a tulip head, and each screwed into a respective pedicle bone of the spine selected from the group consisting of L1-L5; recognizing that the required shape of an attached spinal fixation rod exerts excessive stress on the pedicle bone or the pedicle screw; securing at least one extender 10 to at least one of the tulip heads of at least one of the plurality of pedicle screws; bending a spinal fixation rod to an approximate shape; seating the bent spinal fixation rod into the at least one extender 10; and securing the spinal fixation rod into the at least one extender 10 in the lumbar region of the spine.

A method of use for extenders as described above can be described as a method for securing a spinal fixation rod to a pedicle bone, the method including the following steps: on the cervical region of a spine of a patient in need of orthopedic surgery, providing a plurality of pedicle screws each comprising a tulip head, and each screwed into a respective pedicle bone of the spine selected from the group consisting of C1-C7; recognizing that the required shape of an attached spinal fixation rod exerts excessive stress on the pedicle bone or the pedicle screw; securing at least one extender 10 to at least one of the tulip heads of at least one of the plurality of pedicle screws; bending a spinal fixation rod to an approximate shape; seating the bent spinal fixation rod into the at least one extender 10; and securing the spinal fixation rod into the at least one extender 10 in the cervical region of the spine.

A method of use for extenders as described above can be described as a method for securing a spinal fixation rod to a pedicle bone, the method including the following steps: on the thoracic region of a spine of a patient in need of orthopedic surgery, providing a plurality of pedicle screws each comprising a tulip head, and each screwed into a respective pedicle bone of the spine selected from the group consisting of T1-T12; recognizing that the required shape of an attached spinal fixation rod exerts excessive stress on the pedicle bone or the pedicle screw; securing at least one extender 10 to at least one of the tulip heads of at least one of the plurality of pedicle screws; bending a spinal fixation rod to an approximate shape; seating the bent spinal fixation rod into the at least one extender 10; and securing the spinal fixation rod into the at least one extender 10 in the thoracic region of the spine.

A method of use for extenders as described above can be described as a method for repositioning and securing a spinal fixation rod to a pedicle bone, the method including the following steps: on the lumbar region of a spine of a patient in need of orthopedic surgery, providing a plurality of pedicle screws, each of the pedicle screws comprising a tulip head, and each screwed into a respective pedicle bone of the spine selected from the group consisting of L1-L5; seating a spinal fixation rod into a portion of the tulip heads; recognizing that the required shape of the spinal fixation rod exerts, or will exert, excessive stress on the pedicle bone or the pedicle screw; removing the spinal fixation rod from the portion of the tulip heads; securing at least one extender 10 to at least one of the tulip heads of at least one of the plurality of pedicle screws; re-seating the spinal fixation rod to into the portion of tulip heads, including the at least one extender 10; and securing the spinal fixation rod into the tulip heads, including the at least one extender 10, in the lumbar region of the spine. For each of the methods of use described above involving bending a spinal fixation rod prior to it being secured to an extender 10, the shape of the relevant portion of the spinal fixation rod 122, i.e., at and near the extender 10, can be characterized as wherein the radius of curvature of the bend in the spinal fixation rod is greater when used with an extender 10 relative to the radius of curvature necessary without the use of an extender 10.

A method of use for extenders as described above can be described as a method for repositioning and securing a spinal fixation rod to a pedicle bone, the method including the following steps: on the cervical region of a spine of a patient in need of orthopedic surgery, providing a plurality of pedicle screws, each of the pedicle screws comprising a tulip head, and each screwed into a respective pedicle bone of the spine selected from the group consisting of C1-C7; seating a spinal fixation rod into a portion of the tulip heads; recognizing that the required shape of the spinal fixation rod exerts, or will exert, excessive stress on the pedicle bone or the pedicle screw; removing the spinal fixation rod from the portion of the tulip heads; securing at least one extender 10 to at least one of the tulip heads of at least one of the plurality of pedicle screws; re-seating the spinal fixation rod to into the portion of tulip heads, including the at least one extender 10; and securing the spinal fixation rod into the tulip heads, including the at least one extender 10, in the cervical region of the spine. For each of the methods of use described above involving bending a spinal fixation rod prior to it being secured to an extender 10, the shape of the relevant portion of the spinal fixation rod 122, i.e., at and near the extender 10, can be characterized as wherein the radius of curvature of the bend in the spinal fixation rod is greater when used with an extender 10 relative to the radius of curvature necessary without the use of an extender 10.

A method of use for extenders as described above can be described as a method for repositioning and securing a spinal fixation rod to a pedicle bone, the method including the following steps: on the thoracic region of a spine of a patient in need of orthopedic surgery, providing a plurality of pedicle screws, each of the pedicle screws comprising a tulip head, and each screwed into a respective pedicle bone of the spine selected from the group consisting of T1-T12; seating a spinal fixation rod into a portion of the tulip heads; recognizing that the required shape of the spinal fixation rod exerts, or will exert, excessive stress on the pedicle bone or the pedicle screw; removing the spinal fixation rod from the portion of the tulip heads; securing at least one extender 10 to at least one of the tulip heads of at least one of the plurality of pedicle screws; re-seating the spinal fixation rod to into the portion of tulip heads, including the at least one extender 10; and securing the spinal fixation rod into the tulip heads, including the at least one extender 10, in the thoracic region of the spine. For each of the methods of use described above involving bending a spinal fixation rod prior to it being secured to an extender 10, the shape of the relevant portion of the spinal fixation rod 122, i.e., the at and near the extender 10, can be characterized as wherein the radius of curvature of the bend in the spinal fixation rod is greater when used with an extender 10 relative to the radius of curvature necessary without the use of an extender 10.

A method for securing a spinal fixation rod to a pedicle bone in the lumbar region of a spine of a patient in need of orthopedic surgery to modify the curvature of the lumbar region, the method including the following steps: providing a plurality of pedicle screws, at least one of the pedicle screws comprising a tulip head, and each screwed into a respective pedicle of a vertebrae of the spine selected from the group consisting of L1-L5; providing a pedicle screw extender; reducing a spinal fixation rod at least partially into the tulip head; recognizing that upon full reduction and securing of the spinal fixation rod into the tulip head the spinal fixation rod will exert excessive stress on the respective vertebra; removing the spinal fixation rod from the tulip head; securing the pedicle screw extender to the tulip head; re-reducing the spinal fixation rod into the pedicle screw extender; and securing the spinal fixation rod into the pedicle screw extender.

A method for securing a spinal fixation rod to a pedicle bone of a spine of a patient in need of orthopedic surgery to modify the curvature of the spine, the method including the following steps: providing a tulip head of a pedicle screw; providing a pedicle screw extender; providing a spinal fixation rod; securing the pedicle screw extender to the tulip head of the pedicle screw; seating the spinal fixation rod into the pedicle screw extender; and securing the spinal fixation rod into the pedicle screw extender.

A method for securing a spinal fixation rod to a pedicle bone on the lumbar region of a spine of a patient in need of orthopedic surgery to modify the curvature of the lumbar region, the method including the following steps: providing a pedicle screw comprising a tulip head, the pedicle screw being screwed into a pedicle bone of a vertebrae of the spine selected from the group consisting of L1-L5; providing a pedicle screw extender; recognizing that the required shape of an attached spinal fixation rod exerts excessive stress on the pedicle bone; securing the pedicle screw extender to the tulip head of the pedicle screw; bending a spinal fixation rod to an approximate desired curvature of the lumbar region; seating the spinal fixation rod into the pedicle screw extender; and securing the spinal fixation rod into the pedicle screw extender.

The method of paragraph C wherein the pedicle screw extender comprises: an upper body portion joined to a lower body portion, the upper body portion having two opposing arms extending upwardly from a curved lower surface to define a substantially U-shaped interior channel having a first channel axis, the curved lower surface defining an access opening extending through the upper body portion in a direction generally perpendicular to the first channel axis, the lower body portion extending downwardly as a protrusion from the upper body portion and joined to the upper body portion and having first and second sides, the first and second sides being substantially planar and parallel and separated by an interior portion, the first and second sides defining a protrusion height and a protrusion width, and a screw disposed in the interior portion and having external threads defining a thread diameter greater than the protrusion width.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

We claim:

1. A spinal fixation system, the system comprising:
   a pedicle screw including a shank and a tulip head connected to an end of the shank, the tulip head including a first arm, a second arm, and a tulip head channel defined by and between the first and second arms;
   a pedicle screw tulip head extender including an upper body portion joined to a lower body portion,
   i. the upper body portion having two opposing arms extending upwardly from a curved lower surface to define a substantially U-shaped interior channel having a first channel axis, the curved lower surface defining an access opening extending through the upper body portion in a direction generally perpendicular to the first channel axis,
   ii. the lower body portion extending downwardly as a protrusion from the upper body portion and joined to the upper body portion and having first and second sides, the first and second sides being substantially planar and parallel and separated by an interior portion, the first and second sides defining a protrusion height and a protrusion width, and
   iii. a screw disposed in the interior portion and having external threads defining a thread diameter greater than the protrusion width,
   wherein the lower body portion of the pedicle screw tulip head extender is configured to be disposed within the tulip head channel.

2. The spinal fixation system of claim 1, wherein the lower body portion is substantially a U-shaped protrusion.

3. The spinal fixation system of claim 1, wherein the first and second sides are substantially U-shaped.

4. The spinal fixation system of claim 1, wherein the two opposing arms each comprise complementary first interior threads for receiving a set screw.

5. The spinal fixation system of claim 1, wherein the screw comprises a driving portion accessible through the access opening.

6. The spinal fixation system of claim 1, wherein the upper body portion comprises a pocket for engaging with a rod reducing tool.

7. The spinal fixation system of claim 1, further comprising a pedicle screw, the pedicle screw comprising a tulip head, wherein the lower body portion is secured in the tulip head.

8. The spinal fixation system of claim 1, further comprising a pedicle screw, the pedicle screw comprising a tulip head and interior threads, wherein the external threads of the lower body portion engage the interior threads in the tulip head.

9. The spinal fixation system of claim 1, further comprising a spinal rod configured to be disposed within the U-shaped interior channel.

10. The spinal fixation system of claim 1, further comprising an instrument.

11. The spinal fixation system of claim 10, wherein the instrument is a rod reducer.

12. The spinal fixation system, comprising a mounting rod having a first end and a second end, the mounting rod being generally straight at the first end and defining a central rod axis disposed at a first elevation, the mounting rod being generally turned at an angle on the second end, and having disposed on the second end a rod securing body portion comprising two opposing arms each including a portion of interior threads and extending from a curved lower surface defining a substantially U-shaped interior channel that can have a first channel axis disposed at a second elevation above the first elevation; and
- a pedicle screw including a shank and a tulip head connected to an end of the shank, the tulip head including a first arm, a second arm, and a tulip head channel defined by and between the first and second arms;

wherein a portion of the mounting rod is configured to be disposed within the tulip head channel.

13. The spinal fixation system of claim 12, wherein the mounting rod has a cylindrical cross section.

14. The spinal fixation system of claim 12, wherein the mounting rod is turned at an angle of about 90 degrees.

15. The spinal fixation system of claim 12, wherein the rod securing body portion comprises a pocket for engaging with a rod reducing tool.

16. The spinal fixation system of claim 12, wherein the first channel axis is in a same plane as the central rod axis.

17. The spinal fixation system of claim 12, wherein the first channel axis is in a plane that is substantially perpendicular to the plane of the central rod axis.

18. The spinal fixation system of claim 12, further comprising a spinal rod configured to be disposed within the U-shaped interior channel.

19. The spinal fixation system of claim 18, further comprising a set screw configured to engage the interior threads.

20. The spinal fixation system of claim 12, further comprising an instrument.

* * * * *